(12) United States Patent
Hanada et al.

(10) Patent No.: US 9,664,765 B2
(45) Date of Patent: May 30, 2017

(54) MAGNETIC RESONANCE IMAGING APPARATUS AND GRADIENT MAGNETIC FIELD WAVEFORM ESTIMATION METHOD

(75) Inventors: Hikaru Hanada, Tokyo (JP); Yoshitaka Sato, Tokyo (JP); Kosuke Hirai, Tokyo (JP); Kuniharu Oka, Tokyo (JP); Masahiro Takizawa, Tokyo (JP); Naoya Sakaguchi, Tokyo (JP); Hidehisa Akimaru, Tokyo (JP); Miyuki Kawamura, Tokyo (JP)

(73) Assignee: HITACHI, LTD., Tokyo (JP)

( * ) Notice: Subject to any disclaimer, the term of this patent is extended or adjusted under 35 U.S.C. 154(b) by 714 days.

(21) Appl. No.: 14/128,051

(22) PCT Filed: Jun. 27, 2012

(86) PCT No.: PCT/JP2012/066316
§ 371 (c)(1),
(2), (4) Date: Dec. 20, 2013

(87) PCT Pub. No.: WO2013/002233
PCT Pub. Date: Jan. 3, 2013

(65) Prior Publication Data
US 2014/0125333 A1    May 8, 2014

(30) Foreign Application Priority Data
Jun. 30, 2011    (JP) .................. 2011-146605

(51) Int. Cl.
*G01V 3/00* (2006.01)
*G01R 33/565* (2006.01)
*A61B 5/055* (2006.01)

(52) U.S. Cl.
CPC . *G01R 33/56518* (2013.01); *G01R 33/56572* (2013.01); *A61B 5/055* (2013.01)

(58) Field of Classification Search
CPC ........ G01R 33/56518; G01R 33/56572; A61B 5/055
(Continued)

(56) References Cited

U.S. PATENT DOCUMENTS 6,271,666 B1 * 8/2001 Linz ................. G01R 33/56518
324/309
6,396,268 B1 * 5/2002 Hinks .................. G01R 33/389
324/300
(Continued)

FOREIGN PATENT DOCUMENTS

| JP | 4-54614 | 2/1992 |
| JP | 11-89817 | 4/1999 |
| WO | WO 2010/047245 | 4/2010 |

OTHER PUBLICATIONS

International Search Report in PCT/JP2012/066316, Jul. 2012.

*Primary Examiner* — Susan Lee
(74) *Attorney, Agent, or Firm* — Cooper & Dunham LLP

(57) ABSTRACT

In order to obtain a highly reliable image with no image distortion or no artifacts, such as ghosting, by compensating for the distortion of an output gradient magnetic field waveform caused by various factors with high accuracy, an input gradient magnetic field waveform and an output gradient magnetic field waveform corresponding to the input gradient magnetic field waveform are calculated, a response function that is a sum of response functions of a plurality of elements affecting the output gradient magnetic field waveform is calculated using the input gradient magnetic field waveform and the output gradient magnetic field waveform, an output gradient magnetic field waveform is calculated from an input gradient magnetic field waveform of a gradient magnetic field pulse set in the imaging sequence using the response function, and various kinds of correction are (Continued)

performed using the calculated value of the calculated output gradient magnetic field waveform.

16 Claims, 20 Drawing Sheets

(58) Field of Classification Search
USPC .......................................................... 324/307
See application file for complete search history.

(56) References Cited

U.S. PATENT DOCUMENTS

| | | | | |
|---|---|---|---|---|
| 2004/0097802 | A1* | 5/2004 | Cohen | A61B 5/04004 600/411 |
| 2004/0227513 | A1* | 11/2004 | Weissenberger | G01R 33/3875 324/309 |
| 2011/0200243 | A1 | 8/2011 | Takizawa et al. | |
| 2011/0254624 | A1* | 10/2011 | Onishi | H03F 1/3247 330/149 |

* cited by examiner

FIG. 13
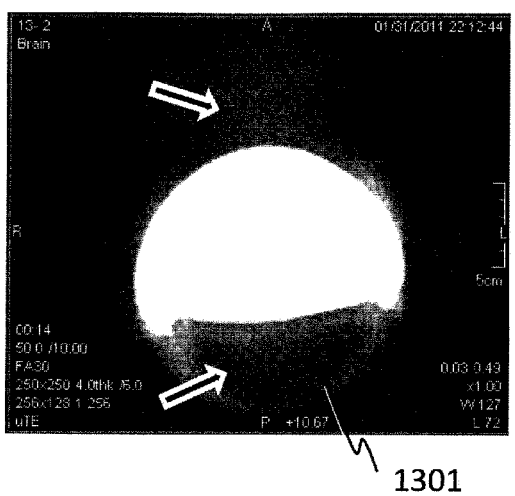
1301
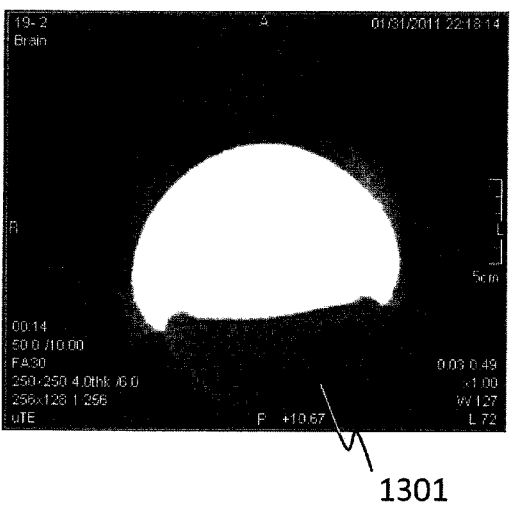
1301

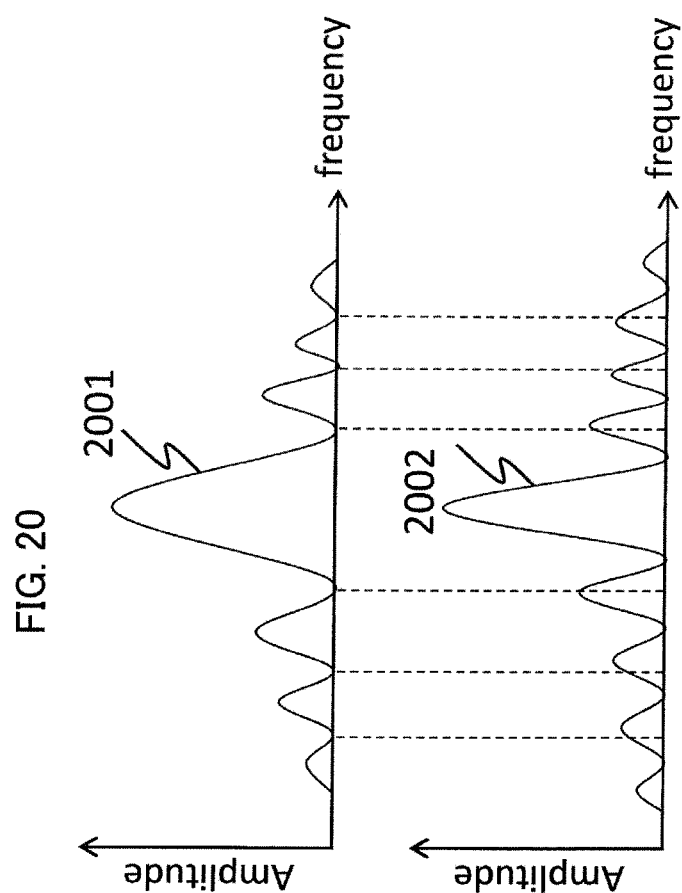

MAGNETIC RESONANCE IMAGING APPARATUS AND GRADIENT MAGNETIC FIELD WAVEFORM ESTIMATION METHOD

TECHNICAL FIELD

The present invention relates to a magnetic resonance imaging (hereinafter, referred to as "MRI") apparatus that measures a nuclear magnetic resonance signal (hereinafter, referred to as an NMR signal) from hydrogen, phosphorus, or the like in an object and images nuclear density distribution, relaxation time distribution, or the like, and in particular, to a technique for compensating for image quality degradation due to distortion of a gradient magnetic field.

BACKGROUND ART

The MRI apparatus is an apparatus that measures an NMR signal generated by an object, especially, the spin of nuclei that form human tissue, and images the shapes or functions of the head, abdomen, limbs, and the like in a two-dimensional manner or in a three-dimensional manner. In imaging, an object is disposed in a static magnetic field (polarized magnetic field B0), and then a high frequency magnetic field pulse is applied together with a slice selection gradient magnetic field pulse in order to selectively excite a specific region. Then, a phase encoding gradient magnetic field pulse or a readout gradient magnetic field pulse is applied for encoding within the excitation range, thereby giving position information.

As for the gradient magnetic field pulse, a desired gradient magnetic field pulse (referred to as an output gradient magnetic field waveform) is output by supplying a current changing in a pulse shape (referred to as an input gradient magnetic field waveform) from a gradient magnetic field power source to a plurality of coils that generates linear gradient magnetic fields in directions of three axes perpendicular to each other. Ideally, an input gradient magnetic field waveform and a gradient magnetic field waveform generated in the MRI apparatus by the input gradient magnetic field waveform should be equal. However, error is caused by various factors.

One of the causes of the error is the influence of the eddy current generated in a magnetic component or an electrical circuit, which forms the MRI apparatus, due to rapid changes in the magnetic field due to the gradient magnetic field pulse. The eddy current causes a change in the magnetic field in the opposite direction to a change in the magnetic field due to the gradient magnetic field pulse depending on time and space, distorting the output gradient magnetic field waveform.

In addition, generally, the output gradient magnetic field waveform of the gradient magnetic field coil includes distortion such as a response delay depending on the characteristics (Q value) of the gradient magnetic field coil. In order to compensate for this, a circuit that performs feedback control and the like is included in a gradient magnetic field generation system including a gradient magnetic field power source in many cases. Such a control circuit plays a role of compensating for the eddy current, but may also be a cause of generating an output gradient magnetic field waveform that is different from the input gradient magnetic field waveform.

Distortion of the output gradient magnetic field waveform caused by the influence of the eddy current and the control circuit of the gradient magnetic field power source changes depending on the shape of the input gradient magnetic field waveform, and various problems occur depending on the application axis of the gradient magnetic field.

For example, distortion of the slice selection gradient magnetic field pulse causes an error in the excitation profile and the excitation position. In particular, the influence of this distortion in the case of a VERSE (variable rate selective excitation) method of applying the high frequency magnetic field pulse while changing the application strength of the gradient magnetic field pulse is large.

Distortion of the readout gradient magnetic field pulse causes distortion or artifacts, such as ghosting, in an image. In particular, the influence of this distortion is noticeable in cases of Echo Planar Imaging (EPI) measurement in which measurement is performed while reversing the application polarity of the readout gradient magnetic field pulse, spiral measurement to scan k-space spirally, ultra-short TE measurement to start scanning from the k-space center, and the like.

In order to solve the above-described problems, it is necessary to compensate for the distortion of the output gradient magnetic field waveform that changes depending on the input gradient magnetic field waveform. As known compensation techniques, methods shown below have been proposed.

One method is to apply a magnetic field for compensating for the eddy current using a shim coil, a gradient magnetic field coil, and the like. This method is to compensate for the distortion of the output gradient magnetic field waveform by measuring a magnetic field, which is caused by the eddy current generated after applying a gradient magnetic field pulse, temporally and spatially and outputting the waveform of a gradient magnetic field pulse to cancel the output characteristics of the eddy current obtained from the measurement result (PTL 1 and PTL 2).

In addition, as a method dedicated to compensating for the distortion of the slice selection gradient magnetic field pulse, a method of changing the irradiation timing of the high frequency magnetic field pulse according to the output gradient magnetic field waveform has been proposed (PTL 3). In this method, degradation of the excitation profile is suppressed by measuring the distortion of the gradient magnetic field pulse, calculating the delay time from the center of gravity of the pulse area, and changing the timing of the high frequency magnetic field pulse and the gradient magnetic field pulse on the basis of the delay time. In addition, a method of eliminating a change in the output gradient magnetic field waveform according to the input gradient magnetic field waveform by using a fixed input gradient magnetic field waveform has also been proposed (NPL 1). In this method, when changing the excitation width of the high frequency magnetic field pulse, the amplitude of the high frequency magnetic field pulse is adjusted instead of changing the input gradient magnetic field waveform.

As a method dedicated to compensating for the distortion of the readout gradient magnetic field pulse, a method of modeling a system response using an RLC circuit, estimating an output gradient magnetic field waveform for an input gradient magnetic field waveform, calculating the coordinate position of the NMR signal in k-space using the result, and compensating for image distortion has been proposed (NPL 2). In this method, coefficients of the modeled expression are determined on the basis of the appearance of the image. In addition, instead of the modeling of the method described above, a method of compensating for image distortion by calculating the coordinate position of the NMR signal in k-space from the result obtained by measuring the gradient magnetic field waveform after the end of imaging has also been proposed (NPL 3).

CITATION LIST

Patent Literature

[PTL 1] JP-A-10-272120
[PTL 2] JP-A-2010-42275
[PTL 3] JP-A-2006-149564

Non Patent Literature

[NPL 1] A. M. Takahashi, Reduction of Slice Select Artifacts in Half Pulse Excitations used in Ultrashort TE (UTE) Imaging, ISMRM2010-4955
[NPL 2] S. H. Cho et al, Compensation of eddy current by an R-L-C circuit model of the gradient system, Proc. Intl. Soc. Nag. Reson. Med. 16:1156 (2008)
[NPL 3] Ethan K. Brodsky et al, Characterizing and Correcting Gradient Errors in Non-Cartesian Imaging: Are Gradient Errors Linear Time-Invariant (LTI)?, Magnetic Resonance in Medicine 62:1466-1476 (2009)

SUMMARY OF INVENTION

Technical Problem

However, the methods of compensating for the output gradient magnetic field waveform described above have the following problems.

First, in the method of outputting the gradient magnetic field pulse to compensate for the eddy current (PTL 1 and PTL 2), there is a problem in that it is difficult and expensive to realize an eddy current correction coil, which completely corrects a magnetic field caused by the eddy current, for the eddy current showing temporally and spatially high-order complex changes. In addition, since the behavior of the control circuit of the gradient magnetic field power source is not taken into consideration, distortion of the output gradient magnetic field waveform cannot be removed completely.

Next, in the method of changing the irradiation timing of the high frequency magnetic field pulse according to the output gradient magnetic field waveform (PTL 3), it is not possible to compensate for nonlinear distortion of the output gradient magnetic field waveform since only the irradiation timing of the high frequency magnetic field pulse is changed. In the method of fixing the input gradient magnetic field waveform (NPL 1), adjusting the amplitude of the high frequency magnetic field pulse using only a specific input gradient magnetic field waveform may cause an increase in SAR (Specific Absorption Rate: reference value indicating the amount of energy accumulated in the object).

In addition, in the method of modeling a system response using an RLC circuit (NPL 2), when the response of the system does not fit into the model expression using the RLC circuit, distortion of the output gradient magnetic field waveform cannot be expressed completely, and image distortion or artifacts, such as ghosting, are left. This can happen, for example, when a complex command, such as feedback control, is given by the gradient magnetic field power source. In addition, since each coefficient of the model expression is determined on the basis of the appearance of the image, there is a problem in that the approximation accuracy of the model expression varies depending on the operator who determines the coefficients.

In the method of measuring a gradient magnetic field waveform after imaging and using the gradient magnetic field waveform for reconstruction (NPL 3), fluctuations due to noise are superimposed since the measured gradient magnetic field waveform is used to calculate the k-space coordinates. When processing, such as filtering, is performed to reduce noise, distortion of the gradient magnetic field waveform due to filtering becomes a problem.

Therefore, it is an object of the present invention to accurately calculate the distortion of the output gradient magnetic field waveform that changes according to the input gradient magnetic field waveform and perform various kinds of correction using the calculated output gradient magnetic field waveform.

Solution to Problem

In order to solve the above-described problems, in the present invention, an input gradient magnetic field waveform and an output gradient magnetic field waveform corresponding to the input gradient magnetic field waveform are calculated, a response function that is a sum of response functions of a plurality of elements affecting the output gradient magnetic field waveform is calculated using the input gradient magnetic field waveform and the output gradient magnetic field waveform, an output gradient magnetic field waveform is calculated from an input gradient magnetic field waveform of a gradient magnetic field pulse set in the imaging sequence using the response function, and various kinds of correction are performed using the calculated value of the calculated output gradient magnetic field waveform. As an example of correction, modification of a high frequency magnetic field pulse set in the imaging sequence and/or modification of the k-space coordinates of a nuclear magnetic resonance signal obtained in the imaging sequence are performed.

Advantageous Effects of Invention

According to the present invention, the response function is calculated in consideration of a plurality of elements affecting the output waveform of the gradient magnetic field, for example, each response function of the eddy current or the control circuit of the gradient magnetic field power source, and the output waveform of the gradient magnetic field is calculated using the response function. Therefore, since it is possible to compensate for not only the eddy current but also the distortion of the gradient magnetic field due to the control circuit, it is possible to suppress image distortion or artifacts such as ghosting, which could not be removed in the related art, without using an expensive gradient magnetic field coil for compensation and the like.

BRIEF DESCRIPTION OF DRAWINGS

FIG. 13 is a diagram showing an image obtained using a high frequency magnetic field pulse before recalculation and a high frequency magnetic field pulse after recalculation.

FIG. 20 is a diagram showing a Laplace transform waveform of a trapezoidal wave shown in FIG. 19.

DESCRIPTION OF EMBODIMENTS

Figure 1:
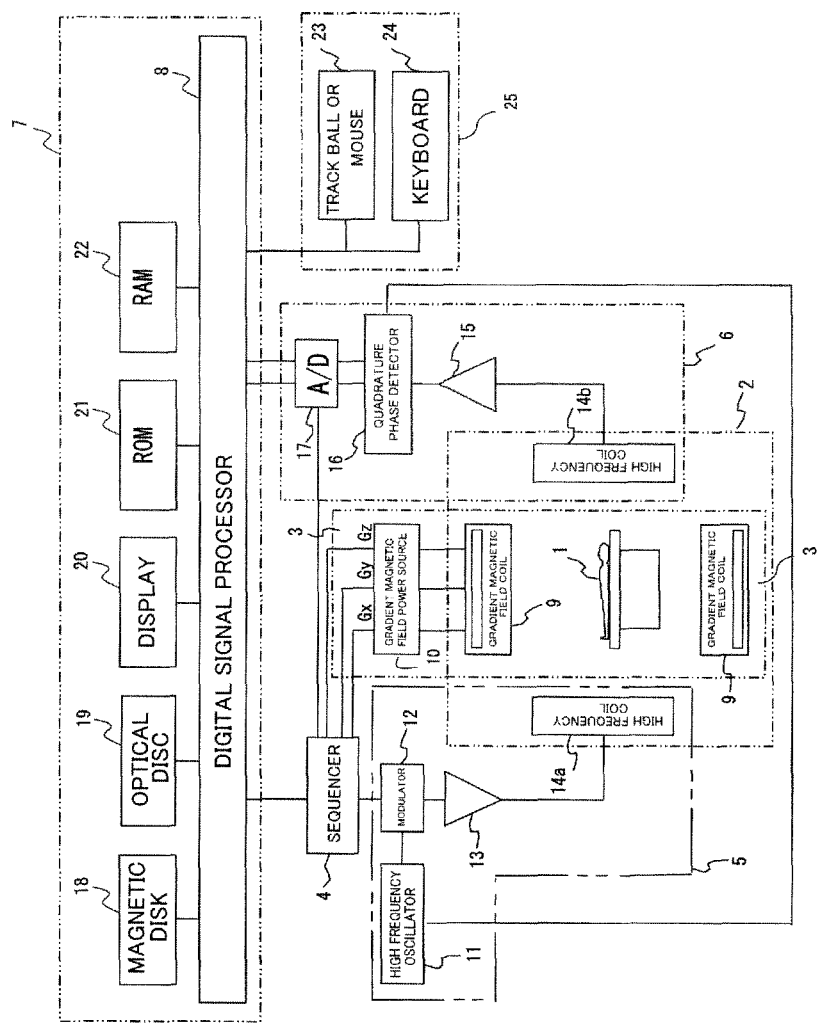
FIG. 1 is a diagram showing the overall configuration of an MRI apparatus.

Hereinafter, preferred embodiments of an MRI apparatus of the present invention will be described in detail according to the accompanying diagrams. In addition, in all diagrams for explaining the embodiments of the invention, the same reference numerals are given to components having the same functions, and repeated explanation thereof will be omitted.

First, a complete overview of an example of an MRI apparatus according to the present invention will be given on the basis of FIG. 1. FIG. 1 is a block diagram showing the overall configuration of an embodiment of the MRI apparatus according to the present invention. The MRI apparatus is intended to obtain a tomographic image of an object using an NMR phenomenon. As shown in FIG. 1, the MRI apparatus is configured to include a static magnetic field generation system 2, a gradient magnetic field generation system 3, a signal transmission system 5, a signal receiving system 6, a signal processing system 7, and a sequencer 4.

Although not shown in the diagram, the static magnetic field generation system 2 includes a static magnetic field generating source, such as a permanent magnet, a normal conducting magnet, or a superconducting magnet, and generates a uniform static magnetic field in space where an object 1 is placed. According to the direction of the static magnetic field, there are a vertical magnetic field type and a horizontal magnetic field type. The static magnetic field generation system 2 generates a uniform static magnetic field in space around the object 1 in a direction perpendicular to the body axis in the case of the vertical magnetic field type and in a body axis direction in the case of the horizontal magnetic field type.

The gradient magnetic field generation system 3 is configured to include gradient magnetic field coils 9 wound in three axial directions of X, Y, and Z, which are the coordinate system (stationary coordinate system) of the MRI apparatus, and a gradient magnetic field power source 10 that drives each of the gradient magnetic field coils and applies gradient magnetic fields Gx, Gy, and Gz in the three axial directions of X, Y, and Z by driving the gradient magnetic field power source 10 of each coil according to a command from the sequencer 4, which will be described later. At the time of imaging, a slice direction gradient magnetic field pulse is applied in a direction perpendicular to the slice surface (imaging cross-section) in order to set the slice surface for the object 1, and a phase encoding direction gradient magnetic field pulse and a frequency encoding direction gradient magnetic field pulse are applied in the two remaining directions, which are perpendicular to the slice surface and are also perpendicular to each other, so that the position information in each direction is encoded in the echo signal.

The sequencer 4 is control unit for repeatedly applying a high frequency magnetic field pulse and a gradient magnetic field pulse according to the predetermined pulse sequence, and operates under the control of the signal processing system 7 (digital signal processor 8) and transmits various commands, which are required to collect the data of a tomographic image of the object 1, to the signal transmission system 5, the gradient magnetic field generation system 3, and the signal receiving system 6. There are various different pulse sequences according to the imaging method, and these are stored on a magnetic disk 18 as a program in advance.

The signal transmission system 5 emits a high frequency magnetic field pulse to the object 1 in order to cause nuclear magnetic resonance in the nuclear spins of atoms that form the body tissue of the object 1, and is configured to include a high frequency oscillator 11, a modulator 12, a high frequency amplifier 13, and a transmission-side high frequency coil (transmission coil) 14a. A high frequency magnetic field pulse output from the high frequency oscillator 11 is amplitude-modulated by the modulator 12 at a timing according to the command from the sequencer 4, and the amplitude-modulated high frequency magnetic field pulse is amplified by the high frequency amplifier 13 and is then supplied to the high frequency coil 14a disposed adjacent to the object 1. As a result, a high frequency magnetic field pulse is emitted to the object 1.

The signal receiving system 6 detects an echo signal (NMR signal) emitted by nuclear magnetic resonance of the nuclear spins, which form the body tissue of the object 1, and is configured to include a receiving-side high frequency coil (receiving coil) 14b, a signal amplifier 15, a quadrature phase detector 16, and an A/D converter 17. The NMR signal of the response of the object 1 induced by the electromagnetic waves emitted from the transmission-side high frequency coil 14a is detected by the high frequency coil 14b disposed adjacent to the object 1 and is amplified by the signal amplifier 15. Then, at a timing according to the command from the sequencer 4, the NMR signal is divided into two signals perpendicular to each other by the quadrature phase detector 16, and each of the signals is converted into a digital amount by the A/D converter 17 and is transmitted to the signal processing system 7.

The signal processing system 7 performs various kinds of data processing, display and storage of processing results, and the like, and includes the digital signal processor 8, external storage devices such as the magnetic disk 18 and an optical disc 19, a display 20, and internal memories such as a ROM 21 and a RAM 22 that store a processing result of the digital signal processor 8 or data used by the digital signal processor 8. When data from the signal receiving system 6 is input to the digital signal processor 8, the digital signal processor 8 executes processing, such as signal processing and image reconstruction, and displays a tomographic image of the object 1, which is the result, on the display 20 and records the tomographic image on the magnetic disk 18 or the like as the external storage device. In addition to the processing such as the image reconstruction described above, the digital signal processor 8 calculates the apparatus characteristics using pre-measurement data or calculates parameters required to execute the pulse sequence stored on the magnetic disk 18, thereby controlling the operation of the sequencer 4.

An operating unit 25 inputs various kinds of control information of the MRI apparatus or control information of processing performed in the signal processing system 7, and is configured to include a track ball or a mouse 23 and a keyboard 24. The operating unit 25 is disposed adjacent to the display 20, so that the operator controls various kinds of processing of the MRI apparatus interactively through the operating unit 25 while watching the display 20.

In addition, in FIG. 1, the transmission-side high frequency coil 14a and the gradient magnetic field coil 9 are provided in the static magnetic field space of the static magnetic field generation system 2, into which the object 1 is inserted, so as to face the object 1 in the case of the vertical magnetic field type and so as to surround the object 1 in the case of the horizontal magnetic field type. In addition, the receiving-side high frequency coil 14b is provided so as to face or surround the object 1.

Figure 2:
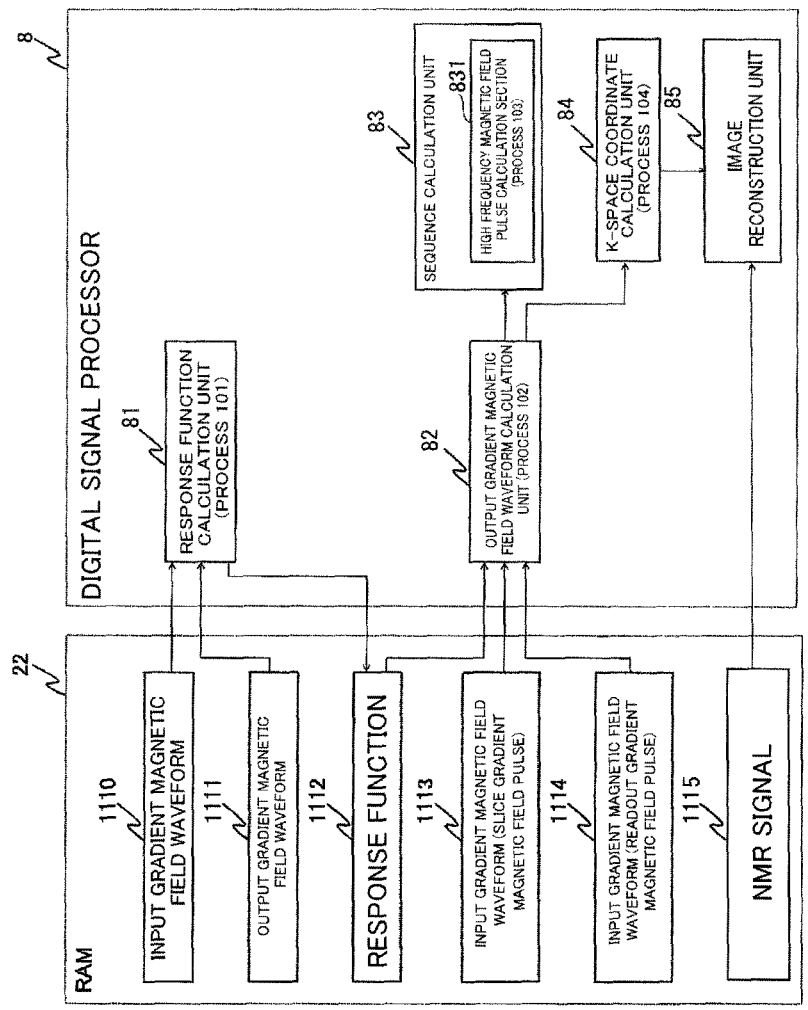
FIG. 2 is a functional block diagram of a digital signal processor.

As a function of the signal processing system 7, the MRI apparatus of the present embodiment further includes a unit for calculating a response function, which indicates the relationship between an input waveform (input gradient magnetic field waveform) input to the gradient magnetic field coil 9 and a gradient magnetic field waveform (output gradient magnetic field waveform) generated in the static magnetic field space by the input waveform, and gradient magnetic field waveform calculation unit for calculating an output gradient magnetic field waveform using the response function. FIG. 2 shows the details of the digital signal processor 8 including these units.

As shown in the diagram, the digital signal processor 8 includes: a response function calculation unit 81 that calculates a response function of the gradient magnetic field; an output gradient magnetic field waveform calculation unit 82 that calculates an output gradient magnetic field waveform of the gradient magnetic field, which is used in the actual imaging sequence, using the calculated response function; a sequence calculation unit 83 that corrects a high frequency pulse and the like, which are used in the imaging sequence, using the output gradient magnetic field waveform calculated by the gradient magnetic field waveform calculation unit 82; a k-space coordinate calculation unit 84 that corrects the coordinate position of k-space where the NMR signal is disposed using the output gradient magnetic field waveform calculated by the gradient magnetic field waveform calculation unit 82; and an image reconstruction unit 85 that creates image data by performing an image reconstruction operation using the NMR signal.

The following explanation will be given focusing on the operation of the MRI apparatus of the present embodiment in the above-described configuration, particularly, focusing on the process performed by the digital signal processor 8.

First Embodiment

The process performed by the digital signal processor 8 of the MRI apparatus of the present embodiment is largely divided into four processes. The relationship of the four processes will be described with reference to the block diagram of FIG. 2. A first process 101 is a process performed by the response function calculation unit 81 as a preliminary measurement, and is a process of calculating response functions 1112 of eddy current and a control circuit of a gradient magnetic field power source. Processes 102 to 104 are processes performed in actual imaging. The process 102 is a process of estimating each output gradient magnetic field waveform using the response function 1112 calculated by the process 101 and input gradient magnetic field waveforms 1113 and 1114 set for each imaging sequence, and is performed by the gradient magnetic field waveform calculation unit 82. The process 103 is a process of recalculating an imaging sequence high frequency magnetic field pulse using the result of the process 102, and is performed by a high frequency magnetic field pulse calculation section 831 of the sequence calculation unit 83. The process 104 is a process of recalculating the k-space coordinates corresponding to each sampling point of a measured NMR signal 1115 using the result of the process 102, and is performed by the k-space coordinate calculation unit 84. Hereinafter, each process will be described in detail.

<<Response Function Calculation Process 101>>

For the process of calculating the response functions of the eddy current and the control circuit of the gradient magnetic field power source in the process 101, the overall flow will be described with reference to the flowchart shown in FIG. 3.

Figure 4:
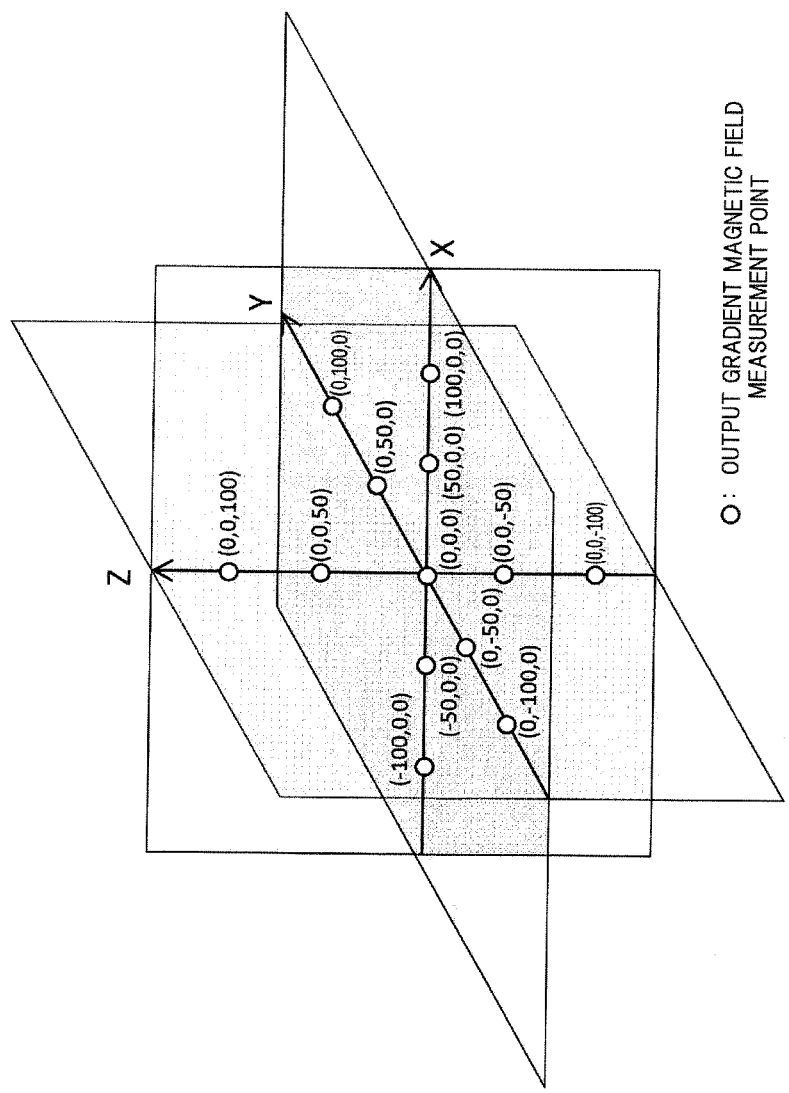
FIG. 4 is a diagram illustrating the measurement of an output gradient magnetic field waveform for each space.

In step 301, setting for disabling the control parameter of the gradient magnetic field power source is performed so that an operation, such as feedback control or feed-forward control, is not performed by the gradient magnetic field power source. In a state where the control of the gradient magnetic field power source is disabled, an output gradient magnetic field waveform is measured for each space in step 302. The output gradient magnetic field can be measured using a known technique (for example, a technique disclosed in PTL 3). For example, as shown in FIG. 4, the measurement for each space is performed at intervals of 50 mm in each axial direction of X, Y, and Z. An output gradient magnetic field waveform 1111 that is the measurement result and an input gradient magnetic field waveform 1110 used at the time of measurement are stored on the RAN 22 (FIG. 1) that is a memory of the signal processing system.

In step 303, the input gradient magnetic field waveform stored on the RAM 22 and the measured output gradient magnetic field waveform are read, and the response function of the eddy current is calculated. A method of calculating the response function of the eddy current will be described later.

Then, in step 304, the control parameter of the gradient magnetic field power source is enabled so that the feedback control, the feed-forward control, or the like can be performed. In this state, the output gradient magnetic field waveform is measured (step 305). This measurement result is also stored on the RAM 22. In step 306, the response function of the control circuit of the gradient magnetic field power source is calculated. A method of calculating the response function of the control circuit of the gradient magnetic field power source will also be described later. The above process is performed for each of the gradient magnetic field coils disposed in the three axial directions of X, Y, and Z.

Figure 5:
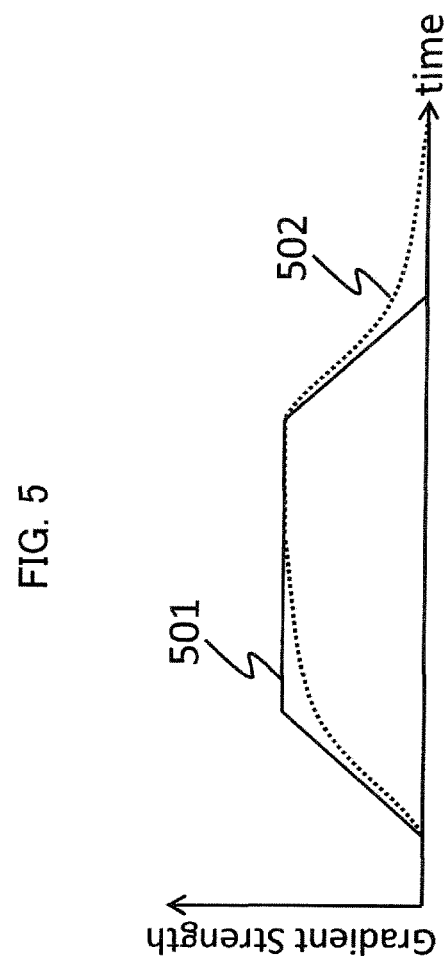
FIG. 5 is a diagram illustrating the distortion of an output gradient magnetic field waveform due to a magnetic field generated by eddy current.

First, calculation of the response function of the eddy current in step 303 will be described. As shown as an example in FIG. 5, a magnetic field generated by the eddy current distorts an output gradient magnetic field waveform 502 with respect to an input gradient magnetic field waveform 501. The relationship between the input gradient magnetic field waveform and the output gradient magnetic field waveform can be expressed by the following expression, for example.

$$Gout(s) - H(s) \times Gin(s) \qquad (1)$$

Here, s is a Laplace variable, Gout(s) is a Laplace transform of the output gradient magnetic field waveform, Gin(s) is a Laplace transform of the input gradient magnetic field waveform, and H(s) is a transfer characteristic of the eddy current. In addition, the output gradient magnetic field waveform is each piece of data measured for each space as shown in FIG. 4. Expression (1) is an example, and can also be replaced with another expression, such as the following expression, for example.

$$Gout(s) - (1-H(s)) \times Gin(s) \qquad (2)$$

In the following description, it is assumed that Expression (1) is used. Since the input gradient magnetic field waveform Gin(s) and the output gradient magnetic field waveform Gout(s) are known, the transfer characteristic H(s) of the eddy current can be calculated from the following expression in theory.

$$H(s) = Gout(s)/Gin(s) \qquad (3.1)$$

The response function of the eddy current is obtained by the inverse Laplace transform of Expression (3.1).

$$h(t) = \text{ILT}[H(s)] \qquad (3.2)$$

Here, ILT[ ] indicates an inverse Laplace transform. Here, in the calculation of Expression (3.1), when the value of Gin(s) is 0, the value of H(s) diverges. Accordingly, a correct value is not obtained. In order to prevent this, in the present embodiment, the correct value is calculated by applying the response function of the eddy current to the model expression and searching for the coefficient in the model expression. An example of the model expression of the response function of the eddy current is shown in the following Expression (4). The response function of this Expression (4) expresses a transient response of the magnetic field generated by the eddy current.

$$h(t) = \alpha_1 \exp(-\tau_1/t) + \alpha_2 \exp(-\tau_2/t) + \ldots + \alpha_n \exp(-\tau_n/t) \qquad (4)$$

Here, t is time, $\alpha_1$ to $\alpha_n$ are amplitude gains, and $\tau_1$ to $\tau_n$ are time constants. The number of exponential functions n in Expression (4) is determined by the type of time constant that each component of the MRI apparatus has. From the experience of the inventor, the transient response of the magnetic field generated by the eddy current can be sufficiently expressed if n is 10.

Figure 6:
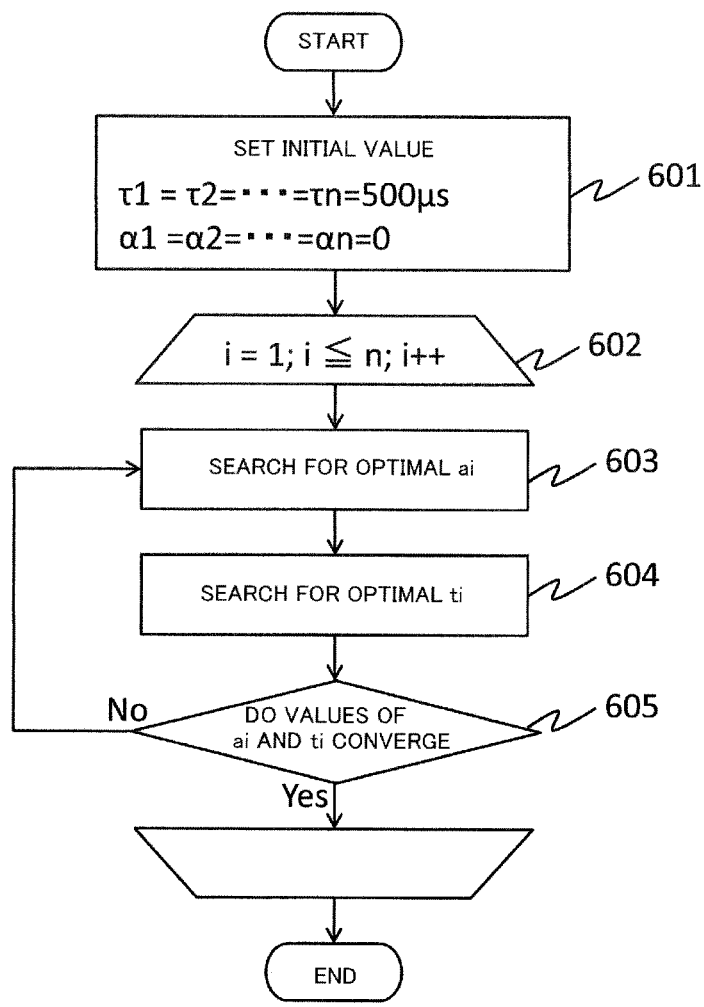
FIG. 6 is a flowchart showing the procedure for calculating the response function of the eddy current in the first embodiment.

In order to calculate the response function of the eddy current, $\alpha_1$ to $\alpha_n$ and $\tau_1$ to $\tau_n$ when the convolution result of the input gradient magnetic field waveform and h(t) of Expression (4) gives a gradient magnetic field waveform closest to the output gradient magnetic field waveform are searched for. The search procedure will be described with reference to the flowchart of FIG. 6.

First, in step 601, the initial values of the amplitude gain and the time constant are set. As the initial values, all coefficients of the amplitude gain α are set to 0 and a positive value other than zero is set as the time constant τ herein. In loop step 602 (repetitive processing), i is set as a loop counter of processing. i corresponds to the number of the subscript of α and τ. That is, in the case of i=1, optimal values of $\alpha_1$ and $\tau_1$ are searched for. In step 603, only $\alpha_1$ is changed to search for the value of optimal $\alpha_1$. In this case, the optimal value is a value when the evaluation value e1 in the following expression becomes a minimum.

$$e1 = \sum_t (gout(t) - h(t) * gin(t))^2 \qquad (5)$$

Here, gout(t) is an output gradient magnetic field waveform, gin(t) is an input gradient magnetic field waveform, and h(t) is a response function shown in Expression (4). Expression (5) shows, in numerical values, how much the convolution result of the response function and the output gradient magnetic field waveform and the convolution result of the response function and the input gradient magnetic field waveform are similar. Therefore, there is no change in essence even if evaluation expressions other than Expression (5) are used. e1 is calculated by changing $\alpha_i$ in the range of $-1 < \alpha_i < 1$ in units of 0.001, and $\alpha_i$ that minimizes e1 is set as an optimal value. Here, it is also possible to use a search algorithm represented by the golden section method or the like.

After setting the searched optimal value $\alpha_i$ to h(t), only $\tau_i$ is changed this time in step 604 to search for the value of $\tau_i$ that minimizes the evaluation amount e1. The search method is the same as for $\alpha_i$. The optimal values of $\alpha_i$ and $\tau_i$ are alternately searched for. Then, in branch step 605, it is determined whether or not the values of $\alpha_i$ and $\tau_i$ converge as a result of continuous update of the values. The convergence condition of $\alpha_i$ and $\tau_i$ can be defined as follows, for example.

$$0.01 > |\alpha_i - \alpha_{i\_prev}| \qquad (6)$$

$$1 \mu s |\tau_i - \tau_{i\_prev}| \qquad (7)$$

Here, $\alpha_{i\_prev}$ and $\tau_{i\_prev}$ are optimal values of $\alpha_i$ and $\tau_i$ detected in previous searches. That is, at least two repeated searches are required.

If the above-described convergence condition is not satisfied, $\alpha_i$ and $\alpha_i$ are searched for again. If the convergence condition is satisfied, i is incremented if i is less than n, and the process proceeds to search for the next combination of $\alpha_i$ and $\tau_i$. If i is equal to or greater than n, the process is ended. In addition, not only the positive value but also the negative value can be taken as α. It is correct that α be a positive value from the generation principle of the eddy current. However, since α1 to αn are calculated in order and the components of α and τ calculated later are neglected to perform a search, a negative value may occur. The response function of the eddy current is calculated in the above procedure.

Figure 7:
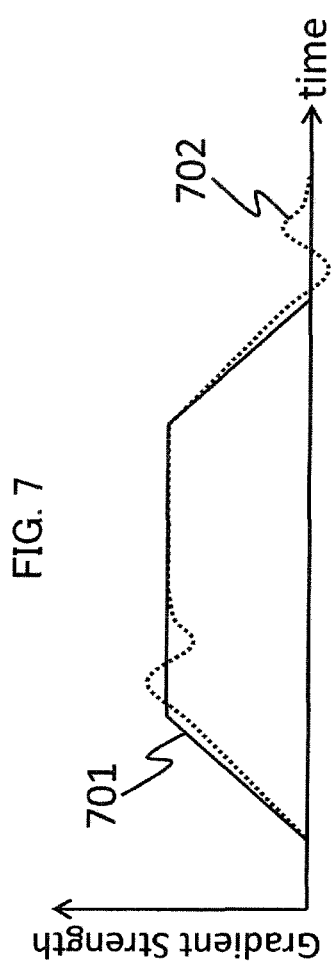
FIG. 7 is a diagram illustrating the overshoot or undershoot added to an output gradient magnetic field waveform by a control circuit of a gradient magnetic field power source.

Next, the calculation of the response function of the control circuit of the gradient magnetic field power source in step 306 of FIG. 3 will be described. As shown as an example in FIG. 7, the control circuit of the gradient magnetic field power source makes a behavior, such as overshoot or undershoot, be included in an output gradient magnetic field waveform 702 compared with an input gradient magnetic field waveform 701. The gradient magnetic field pulse output from the gradient magnetic field power source includes the input waveform and the component from the control circuit, and can be expressed by the following expression.

$$\text{gamp}(t) = \text{gin}(t) + u(t) \tag{8}$$

Here, gamp(t) is a gradient magnetic field pulse output from the gradient magnetic field power source, gin(t) is an input gradient magnetic field waveform, and u(t) is a control component of the gradient magnetic field power source.

This control component is also defined by the model expression as in the case of the eddy current. The model expression of the control component can be appropriately defined according to a control method that the control circuit adopts. As the control method, PID control, P control or PD control that is simpler than the PID control, PI control, or intelligent control, such as a complex neural network, can be assumed. It is preferable to select a control theory according to the specifications of the gradient magnetic field power source mounted in the MRI apparatus to which the present invention is applied. In the present embodiment, a case is assumed in which the control circuit of the gradient magnetic field power source performs PID control, and u(t) is defined by the following model expression.

$$u(t) = K_P \text{Diff}(t) + K_I \int \text{Diff}(t)dt + K_D \frac{d}{dt}\text{Diff}(t) \tag{9}$$

Here, $K_P$ is a proportional gain, $K_I$ is an integral gain, and $K_D$ is a derivative gain. In addition, Diff(t) of Expression (9) is defined by the following expression.

$$\text{Diff}(t) = \text{gin}(t-\text{delay}) - \text{gout}(t-\text{delay}) \tag{10}$$

Here, delay is a time delay when calculating the input of the PID control. The relationship between gamp(t) and the output gradient magnetic field waveform is as follows.

$$\text{gout}(t) = h(t) * \text{gamp}(t) = h(t) * (\text{gin}(t) + u(t)) \tag{11}$$

Figure 3:
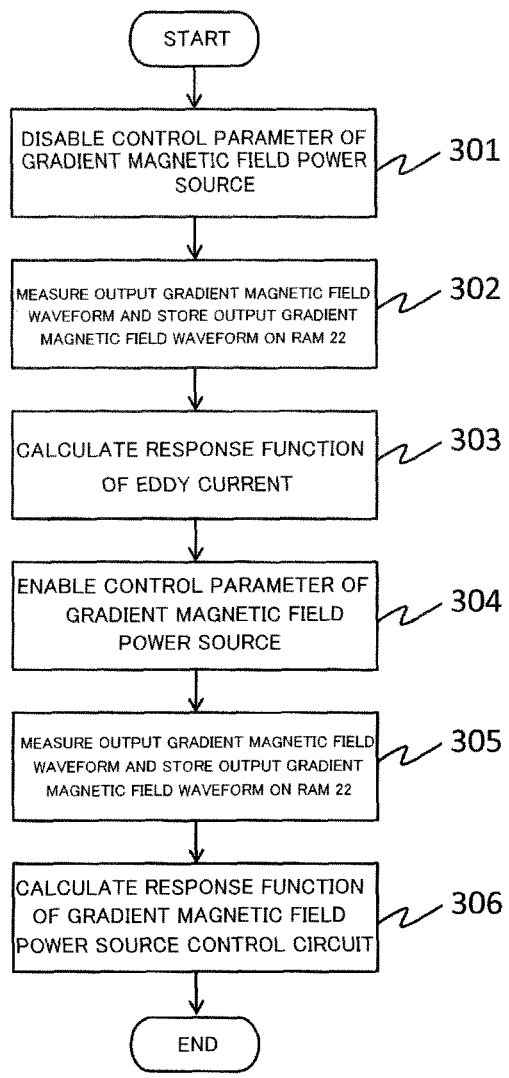
FIG. 3 is a flowchart showing the overall procedure according to a first embodiment.
Figure 8:
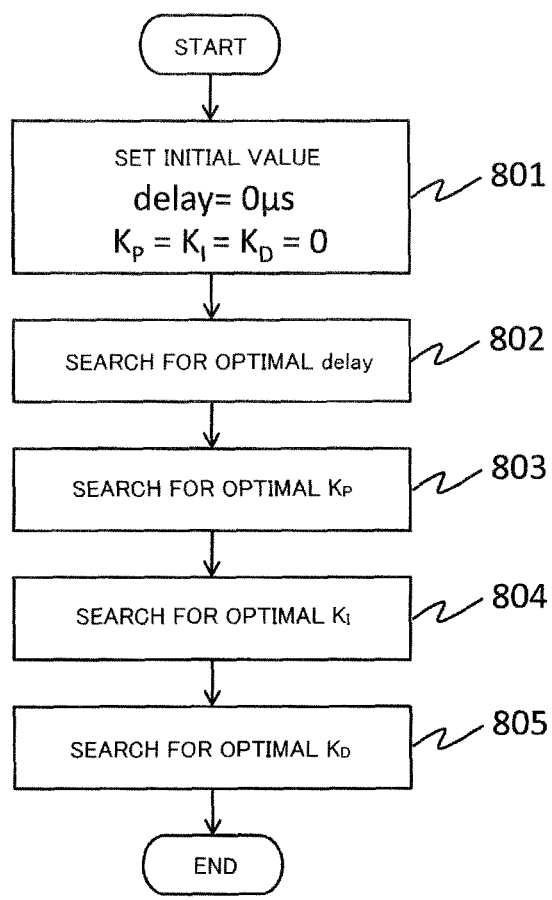
FIG. 8 is a flowchart showing the procedure for calculating the response function of the control circuit of the gradient magnetic field power source in the first embodiment.

Here, gout(t) is an output gradient magnetic field waveform stored on the RAM 22 in step 305 of FIG. 3. h(t) is a response function of the eddy current shown in Expression (4), and is calculated by the processing described above and is known. Therefore, at the time of convolution of gamp(t), which is a sum of the input gradient magnetic field waveform and the control component u(t) of the gradient magnetic field power source, and h(t) calculated in step 303, u(t) that gives a gradient magnetic field waveform closest to the output gradient magnetic field waveform gout (t) is calculated. The procedure of searching for delay, $K_P$, $K_I$, and $K_D$ included in u(t) will be described with reference to the flowchart of FIG. 8. In step 801, all of delay, $K_P$, $K_I$, and $K_D$ are initialized to zero. In step 802, only delay is changed to search for the optimal delay. In this case, the optimal value is a value that minimizes the evaluation amount e2 in the following expression.

$$e2 = \sum_t (\text{gout}(t) - h(t) * \text{gamp}(t))^2 \tag{12}$$

The search for the delay that minimizes the evaluation amount e2 is performed in the same manner as the search processing of the coefficients $\alpha_1$ to $\alpha_n$ and $\tau_1$ to $\tau_n$ of the response function described above. That is, it is possible to perform all-points search within a specific range, or it is possible to use a search algorithm represented by the golden section method or the like. By calculating the delay, Diff(t) is calculated. Then, in step 803, the optimal $K_P$ is searched for. The condition of the optimal $K_P$ is also a value that minimizes the evaluation amount e2 in Expression (12) herein. In the same processing, $K_I$ is searched for in step 804, and $K_D$ is searched for in step 805. The response function of the control circuit of the gradient magnetic field power source obtained finally is expressed by the following expression.

$$h_{PID}(t) = ILT\left[\frac{L[\text{gin}(t) + u(t)]}{L[\text{gin}(t)]}\right] \tag{13}$$

Since the response function h(t) of the eddy current and the response function (control component u(t)) of the control circuit are calculated by the above processing, the output gradient magnetic field waveform can be calculated from Expression (11) if the input gradient magnetic field waveform is given. Parameters of the response functions h(t) (Expression (4)) and u(t) for solving Expression (11) are calculated for each piece of data measured for each space shown in FIG. 4, are stored on the RAM 22 of the signal processing system 7, and are used in pulse sequence calculation or image reconstruction in actual imaging.

Figure 9:
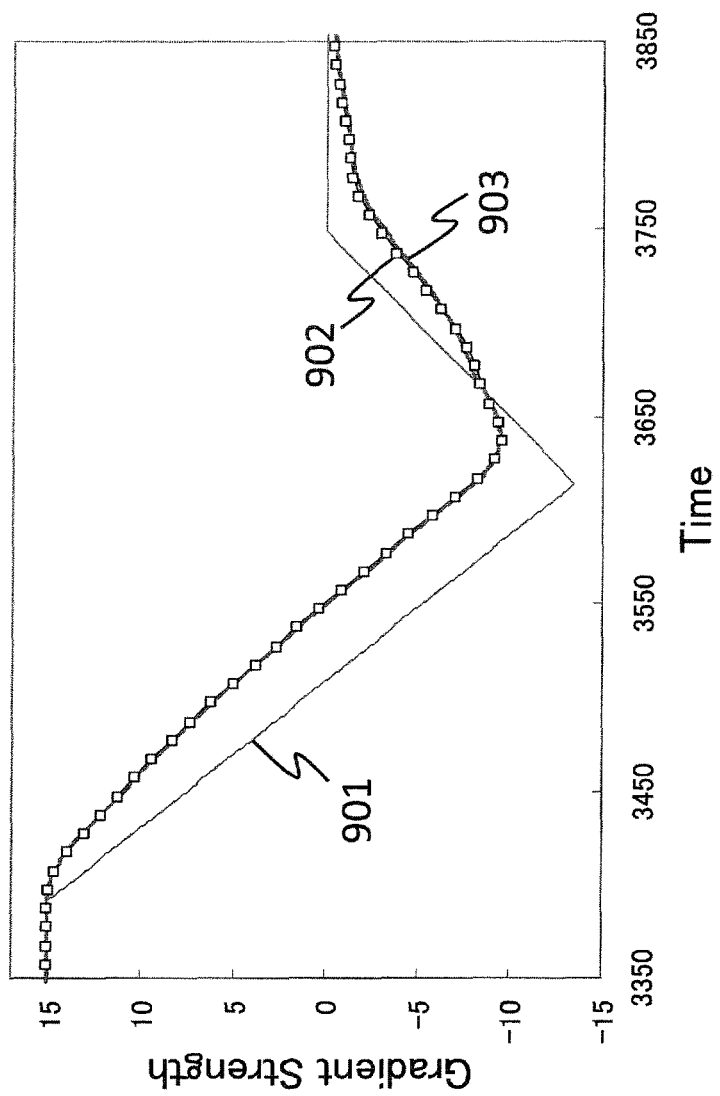
FIG. 9 is a graph showing an output gradient magnetic field waveform estimated using a response function of the first embodiment, an input magnetic field waveform, and an actual output gradient magnetic field waveform.
Figure 10:
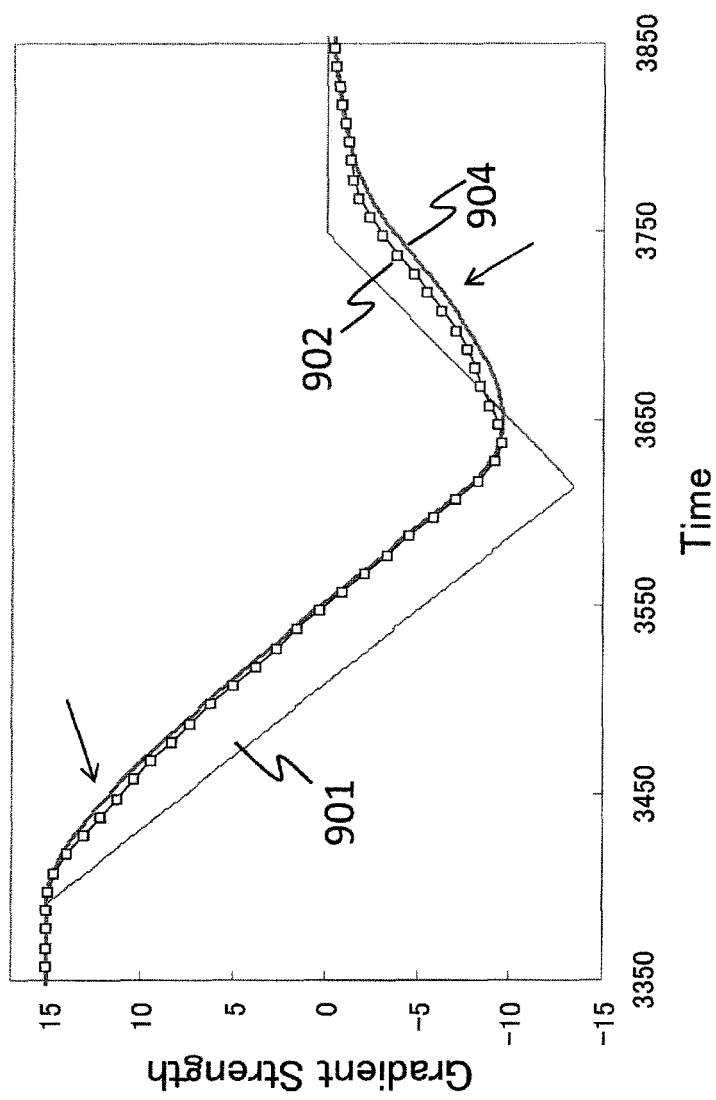
FIG. 10 is a graph showing an output gradient magnetic field waveform estimated using a response function in consideration of only the eddy current, an input magnetic field waveform, and an actual output gradient magnetic field waveform.

FIG. 9 shows an example of the estimation result of the output gradient magnetic field waveform using Expression (11). In this diagram, a waveform 901 is an input gradient magnetic field waveform, a waveform 902 is an output gradient magnetic field waveform obtained by measuring the waveform 902, and a waveform 903 is an output gradient magnetic field waveform estimated using Expression (11). Since the waveforms 902 and 903 match each other satisfactorily, it can be seen that the output gradient magnetic field waveform can be estimated with high accuracy by Expression (11). On the other hand, FIG. 10 is an example of the estimation result of the output gradient magnetic field waveform when the control component u(t) of the gradient magnetic field power source is not added. Between the output gradient magnetic field waveform 902 obtained by actual measurement and the output gradient magnetic field waveform 904 estimated from Expression (11) when u(t) is set to 0, deviation occurs in a portion indicated by the arrow. From this, it can be seen that the output gradient magnetic field waveform cannot be estimated with high accuracy unless the control component of the gradient magnetic field power source is taken into consideration.

<<Output Gradient Magnetic Field Waveform Calculation Process 102>>

Next, referring back to the block diagram of FIG. 2, the process 102 performed by the output gradient magnetic field waveform calculation unit 82 will be described. In actual imaging, an imaging pulse sequence is calculated according to the purpose of the imaging by the sequence calculation unit 83, and a high frequency pulse (amplitude, envelope), a slice selection gradient magnetic field pulse (input gradient magnetic field waveform 1113), a readout gradient magnetic field pulse (input gradient magnetic field waveform 1114), and the like that are included in the calculated imaging pulse sequence are stored on the RAM 22.

Figure 11:
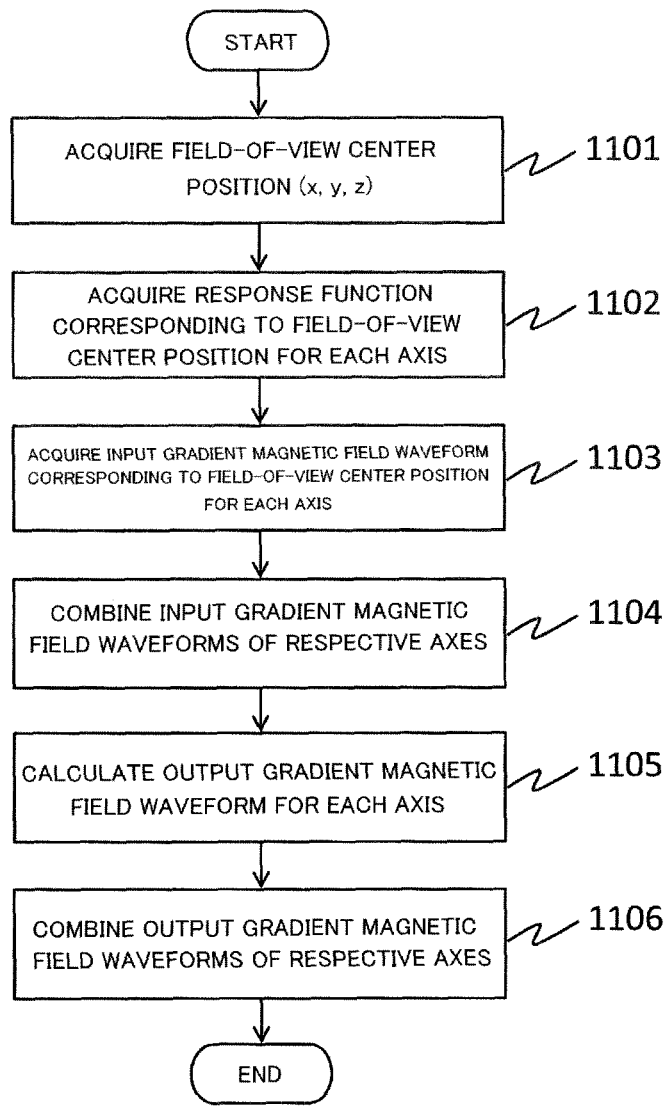
FIG. 11 is a flowchart of the process of estimating an output gradient magnetic field waveform in the first embodiment.

In the process 102, the output gradient magnetic field waveform of the imaging pulse sequence is calculated using the response function 1112 calculated by the response function calculation unit 81 and the set input gradient magnetic field waveforms 1113 and 1114. FIG. 11 shows a flowchart of the process of calculating an output gradient magnetic field waveform.

First, in step 1101, a field-of-view center position in the three axial directions of X, Y, and Z is acquired from the coordinate position of the imaging field of view. The field-of-view center position is calculated from the following expression.

$$CenterPosition(\text{Axis}) = \frac{FOV(\text{Axis, min}) + FOV(\text{Axis, max})}{2} \quad (14)$$

Here, Axis indicates each axis of X, Y, and Z (the same hereinbelow), and FOV (Axis, min) and FOV (Axis, max) are the minimum coordinate position and the maximum coordinate position of the imaging field of view of each axis designated according to the imaging conditions.

In step 1102, the response function h(t) and the control component u(t) corresponding to the field-of-view center position of each axis acquired in step 1101 are selected and acquired from the response function h(t) and the control component u(t) of the gradient magnetic field power source for each space stored on the RAM 22. Here, for the acquisition of the response function h(t) and the control component u(t) of the gradient magnetic field power source, a result calculated at a position closest to the field-of-view center position may be acquired, or the response function h(t) and the control component u(t) of the gradient magnetic field power source may be calculated by interpolating the results calculated for each space. The interpolation is performed according to the following expression.

$$h(\text{Axis}, t) = \frac{P2}{P2 - P1} \cdot h(\text{Axis}, P1, t) + \frac{P1}{P2 - P1} \cdot h(\text{Axis}, P2, t) \quad (15\text{-}1)$$

$$u(\text{Axis}, t) = \frac{P2}{P2 - P1} \cdot u(\text{Axis}, P1, t) + \frac{P1}{P2 - P1} \cdot u(\text{Axis}, P2, t) \quad (15\text{-}2)$$

Here, h(Axis, t) and u(Axis, t) are a response function and a control component of the gradient magnetic field power source circuit at the field-of-view center position of each axis. In addition, P1 and P2 indicate calculated positions of the response function and the control component of the gradient magnetic field power source circuit that are closest in the longitudinal direction of the field-of-view center position.

Then, in step 1103, input gradient magnetic field waveforms in the three axial directions of X, Y, and Z are acquired. The input gradient magnetic field waveform is set according to the imaging pulse sequence and is stored on the RAM 22, and is the slice gradient magnetic field pulse 1113 or the readout gradient magnetic field pulse 1114 shown in FIG. 2. In any case, the content of processing is the same.

In step 1104, a waveform obtained by combining the input gradient magnetic field waveforms of the three axes expressed by the following expression is calculated.

$$gin(t) = \sqrt{gin(X,t)^2 + gin(Y,t)^2 + gin(Z,t)^2} \quad (16)$$

Here, gin(Axis, t) is an acquired input gradient magnetic field waveform of each axis.

In step 1105, an output gradient magnetic field waveform is estimated using the response function h(t) and the control component u(t) of the gradient magnetic field power source for the input gradient magnetic field waveform of each axis. The estimation of the output gradient magnetic field waveform is expressed by the following expression as a form in which Expression (11) is extended to the three axes.

$$gest(\text{Axis},t) = h(\text{Axis},t)*gamp(\text{Axis},t) = h(\text{Axis},t)*(gin(\text{Axis},t) + u(\text{Axis},t)) \quad (17)$$

Here, gest (Axis, t) is an estimation result of the output gradient magnetic field waveform of each axis obtained by calculation. After calculating the output gradient magnetic field waveform of each axis, the waveform of each axis is combined according to the following expression in step 1106.

$$gest(t) = \sqrt{gest(X,t)^2 + gest(Y,t)^2 + gest(Z,t)^2} \quad (18)$$

The output gradient magnetic field waveforms of the slice gradient magnetic field and the readout gradient magnetic field estimated as described above are used in the recalculation (FIG. 2: 103) of the high frequency magnetic field pulse and the correction (FIG. 2: process 104) of the k-space coordinate position of the NMR signal, respectively.

<High Frequency Magnetic Field Pulse Calculation Process 103>>

In the process 103, a high frequency magnetic field pulse is recalculated using the input gradient magnetic field waveform gin(t) and the output gradient magnetic field waveform gest(t) of the slice gradient magnetic field calculated by the output gradient magnetic field waveform calculation unit 82. In the recalculation of the high frequency magnetic field pulse, the envelope and frequency of the high frequency pulse are calculated according to the following expressions.

$$RF'_{env}(t) = RF_{env}(t') \times \frac{gest(t)}{gin(t)} \quad (19)$$

$$RF'_{freq}(t) = RF_{freq}(t') \times \frac{gest(t)}{gin(t)} \quad (20)$$

$$t' = t \times \frac{\sum_{j=0}^{t} gin(j)}{\sum_{j=0}^{t} gest(j)} \quad (21)$$

Here, $RF_{env}'(t)$ is an envelope of a high frequency magnetic field pulse after recalculation, $RF_{env}(t)$ is an envelope of a high frequency magnetic field pulse before recalculation, $RF_{freq}'(t)$ is a frequency of the high frequency magnetic field pulse after recalculation, and $RF_{freq}(t)$ is a frequency of the high frequency magnetic field pulse before recalculation.

As can be seen from these Expressions (19) to (21), the amplitude, frequency, and irradiation time of the envelope of the high frequency magnetic field pulse are changed in proportion to the strength of the output gradient magnetic field waveform of the slice gradient magnetic field herein. On the basis of these expressions, it is possible to perform changes in consideration of the imaging conditions and constraints of the apparatus.

As an example that requires a change, it may be difficult to change the frequency of the high frequency magnetic field pulse with time due to the configuration of the apparatus. In this case, it is possible to realize the modulation of a frequency as a result by changing the phase of the high frequency magnetic field pulse with time. The phase for realizing the frequency modulation is calculated according to the following expression.

$$RF_{phase}(t) = \frac{gest(t)}{g\_standard} \times \text{distance} \times \gamma \times \Delta t \times 2\pi \quad (22)$$

Here, g_standard is a gradient magnetic field strength [T/m] as a reference for calculating the frequency of a high frequency magnetic field pulse, distance is a distance [m] from the magnetic field center to the excitation position, γ is a gyromagnetic ratio [Hz/T], and Δt is a phase change interval time [s] of a high frequency magnetic field pulse.

Here, since a range where the phase can be changed is 0 to 360[°], the range of the distance is also limited. Therefore, in order to increase the setting range of distance, it is preferable that a phase change be small. Therefore, in order to minimize the phase change, g_standard and the frequency of the high frequency magnetic field pulse are calculated according to the following expressions.

$$g\_standard = \text{Average}[gest(t)] \quad (23)$$

$$RF'_{freq} = RF_{freq} \times \frac{\text{Average}[gest(t)]}{\text{Average}[gin(t)]} \quad (24)$$

Here, Average[ ] is average value calculation processing in a high frequency magnetic field pulse application section, $RF_{freq}'$ is a frequency of the high frequency magnetic field pulse after recalculation with no time change, and $RF_{freq}$ is a frequency of the high frequency magnetic field pulse before recalculation with no time change. By calculating g_standard and $RF_{freq}'$ using Expressions (23) and (24), a phase change is minimized. As a result, it is possible to take a large upper limit of distance.

Figure 12:
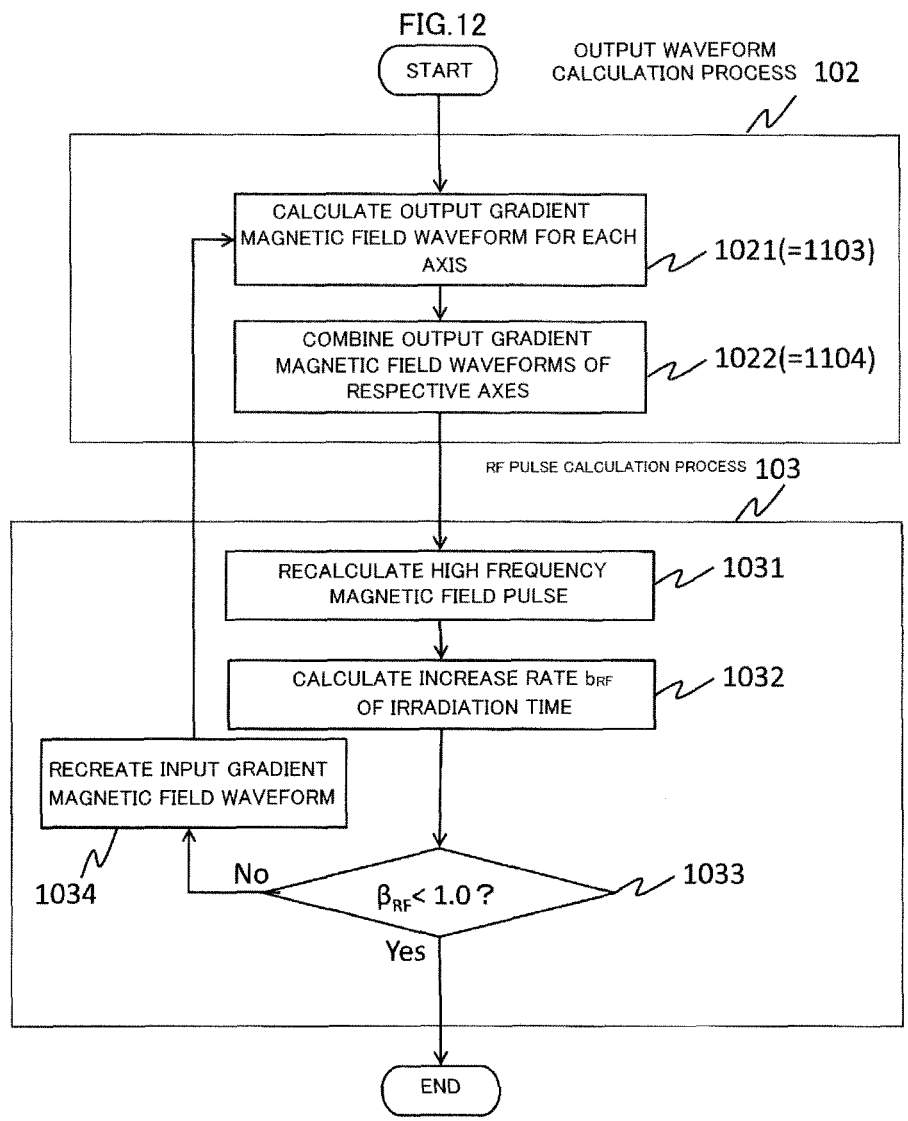
FIG. 12 is a flowchart showing the procedure for recalculating an input gradient magnetic field waveform and a high frequency magnetic field pulse in the first embodiment.

As another example that requires a change, there is a suppression of the irradiation time of the high frequency magnetic field pulse. As a result of recalculation of a high frequency magnetic field pulse using the above Expressions (19) to (21), the irradiation time of the high frequency magnetic field pulse changes. However, depending on the pulse sequence, a change in irradiation time, especially, the extension of irradiation time may be undesirable. The procedure of recalculating the high frequency magnetic field pulse without changing the irradiation time will be described with reference to the flowchart shown in FIG. 12.

In steps 1021 and 1022, calculation of the output gradient magnetic field waveform for each axis and combination of the output gradient magnetic field waveform of each axis are performed. These processes are performed by the output gradient magnetic field waveform calculation unit 82, and are the same as the processes performed in steps 1103 and 1104 of FIG. 11. Then, in step 1031, a high frequency magnetic field pulse is calculated according to Expressions (19) to (21). In response to the result, an increase rate $\beta_{RF}$ of irradiation time is calculated in step 1032. The increase rate $\beta_{RF}$ is calculated according to the following expression.

$$\beta_{RF} = \frac{\sum_{t=StarTime}^{EndTime} gin(t)}{\sum_{t=StarTime}^{EndTime} gest(t)} \quad (25)$$

Here, gin(t) is an input gradient magnetic field waveform, gest(t) is an estimation result of an output gradient magnetic field waveform calculated from Expression (18), and Start-Time is a high frequency magnetic field pulse irradiation start time, and EndTime is a high frequency magnetic field pulse irradiation end time.

In branch step 1033, it is determined whether or not the increase rate $\beta_{RF}$ exceeds 1.0. When the increase rate $\beta_{RF}$ exceeds 1.0, the irradiation time of the high frequency magnetic field pulse after calculation is extended.

In this case, the process proceeds to step 1034, in which the input gradient magnetic field waveform of the slice gradient magnetic field is recreated. The input gradient magnetic field waveform is recreated according to the following expression.

$$gin'(t) = gin(t) \cdot \beta_{RF} \quad (26)$$

By multiplying the input gradient magnetic field waveform by the irradiation time increase rate $\beta_{RF}$, the strength of the input gradient magnetic field waveform is increased. As a result, the application time of the high frequency magnetic field pulse is shortened. In this case, since the entire input gradient magnetic field waveform is only increased uniformly, no special shim coil, gradient magnetic field coil, and the like are required.

After the recreation of the input gradient magnetic field waveform, the process returns to step 1021 of the process 102 with the result as an input, and calculation of the output gradient magnetic field waveform (steps 1021 and 1022), recalculation of the high frequency magnetic field pulse (step 1031), and calculation of the irradiation time increase rate $\beta_{RF}$ (step 1032) are performed. The process is ended if the irradiation time increase rate $\beta_{RF}$ calculated again is equal to or less than 1.0, and the input gradient magnetic field waveform is created again if the irradiation time increase rate $\beta_{RF}$ calculated again is not equal to or less than 1.0. In this case, gin(t) of Expression (26) is an input gradient magnetic field waveform recreated immediately before.

By repeating the recreation of the input gradient magnetic field waveform of the slice gradient magnetic field in this manner, the irradiation time of the high frequency magnetic field pulse cannot be extended eventually compared with the irradiation time of the high frequency magnetic field pulse before recalculation. As a result, when using a high frequency magnetic field pulse after recalculation, it is not necessary to change any pulse sequence excluding the slice gradient magnetic field pulse.

FIG. 13 is an image 1301 obtained using a high frequency magnetic field pulse before recalculation and an image 1302 obtained using a high frequency magnetic field pulse after recalculation. Both the images are imaging results in ultra-short TE measurement using a VERSE method. Compared with the image 1301 obtained using the high frequency magnetic field pulse before recalculation, the image 1302 obtained using the high frequency magnetic field pulse after recalculation has a small amount of mixing of a background signal (signal other than signals from the imaging cross-section) indicated by the arrow. Accordingly, it can be seen that a good excitation profile is obtained in the image 1302.

<<k-Space Coordinate Recalculation Process 104>>

Figure 14:
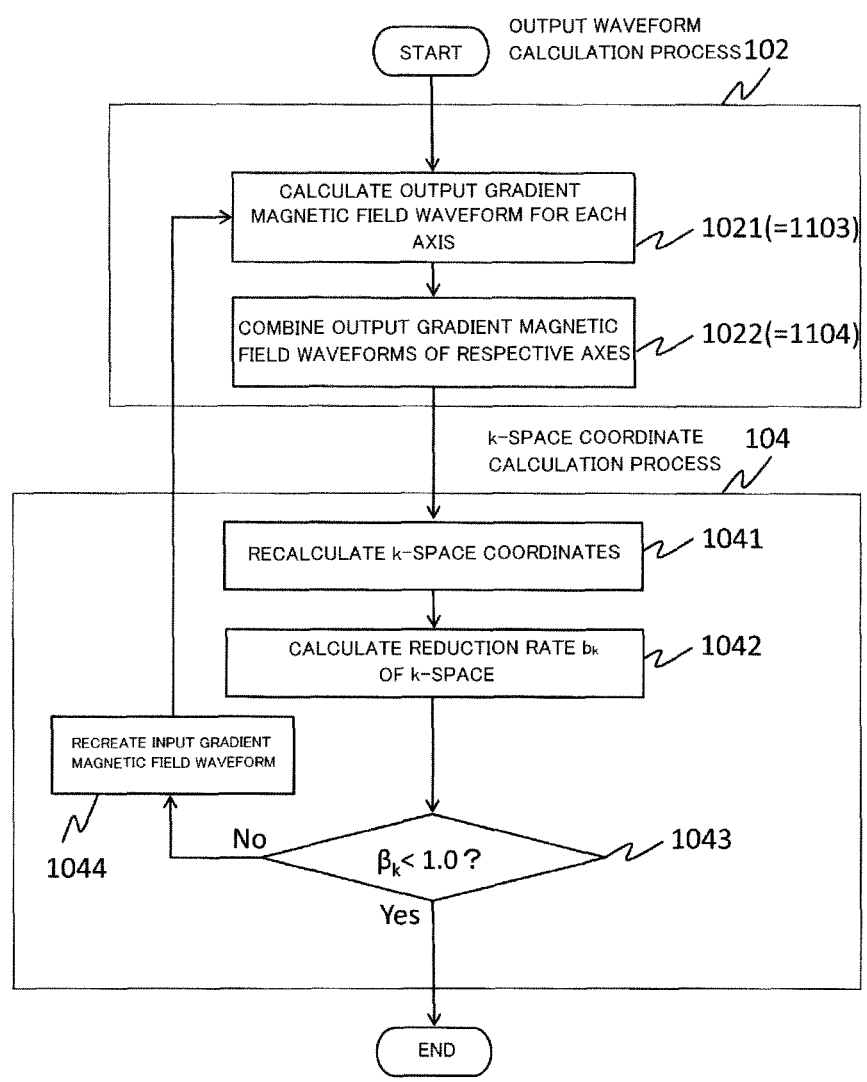
FIG. 14 is a flowchart showing the procedure for recalculating an input gradient magnetic field waveform and k-space coordinates in the first embodiment.

Subsequently, the k-space coordinate recalculation process 104 performed by the k-space coordinate calculation unit 84 shown in FIG. 2 will be described. In the k-space coordinate recalculation process 104, k-space coordinates at which an NMR signal is disposed are recalculated using the input gradient magnetic field waveform gin(t) and the output gradient magnetic field waveform gest(t) of the readout gradient magnetic field calculated by the output gradient magnetic field waveform calculation unit 82. FIG. 14 shows an example of the flowchart showing the recalculation procedure of k-space coordinates. This procedure is also the flow of a process similar to the flowchart of the recalculation of the high frequency magnetic field pulse shown in FIG. 12, and the input gradient magnetic field waveform of the readout gradient magnetic field is recreated by the recalculation result of the k-space coordinates.

First, in step 1041, k-space coordinates are calculated using the input gradient magnetic field waveform gin(t) and the output gradient magnetic field waveform gest(t) of the readout gradient magnetic field that have been calculated in the process 102. The recalculation of the k-space coordinates using the output gradient magnetic field waveform gest(t) is performed according to the following expression.

$$k'(t) = \gamma \sum_{j=0}^{t} gest(j) \quad (27)$$

Here, $\gamma$ is a gyromagnetic ratio [Hz/T]. This expression is obtained by replacing gin(j) of expression (following Expression (28)) for calculating the k-space coordinates using the general input gradient magnetic field waveform gin(t) with gest(j).

$$k(t) = \gamma \sum_{j=0}^{t} gin(j) \quad (28)$$

Then, it is checked whether or not the range of the coordinates calculated by recalculation has been reduced. The range of the recalculated k-space coordinates k'(t) may be reduced from the range of the original k-space coordinates k(t). In this case, since no signal is filled within the range assumed in k-space, the resolution of the image is reduced. Therefore, in step 1042, the reduction rate $\beta_k$ of k-space is calculated.

The reduction rate $\beta_k$ is calculated according to the following expression.

$$\beta_k = \frac{k'(EndTime)}{k(EndTime)} \quad (29)$$

Here, EndTime indicates an application end time of a readout gradient magnetic field pulse (or measurement end time of an NMR signal).

In branch processing step 1043, it is determined whether or not the reduction rate $\beta_k$ is less than 1.0. When the reduction rate $\beta_k$ is less than 1.0, the k-space coordinates after recalculation k'(t) are reduced from the k-space coordinates before recalculation k(t). In this case, the process proceeds to step 1044, in which the input gradient magnetic field waveform of the readout gradient magnetic field is recreated. The input gradient magnetic field waveform is recreated according to the following expression.

$$gin'(t) = \frac{gin(t)}{\beta_k} \quad (30)$$

By multiplying the input gradient magnetic field waveform by the reciprocal of the reduction rate $\beta_k$ of irradiation time, the strength of the input gradient magnetic field waveform is increased. As a result, the range of the k-space coordinates is increased. In this case, since the entire input gradient magnetic field waveform is only increased uniformly as can be seen from Expression (30), no special shim coil, gradient magnetic field coil, and the like are required. After the recreation of the input gradient magnetic field waveform, the process returns to the process 102 with the result as an input, and calculation of the output gradient magnetic field waveform (steps 1021 and 1022), recalculation of the k-space coordinates (step 1041), and calculation of the reduction rate $\beta_k$ (step 1042) are performed.

In branch processing step 1043, the process is ended if the reduction rate $\beta_k$ calculated again is equal to or greater than 1.0, and the input gradient magnetic field waveform is created again if the reduction rate $\beta_k$ calculated again is not equal to or greater than 1.0. In this case, gin(t) of Expression (30) is an input gradient magnetic field waveform recreated immediately before.

Figure 15:
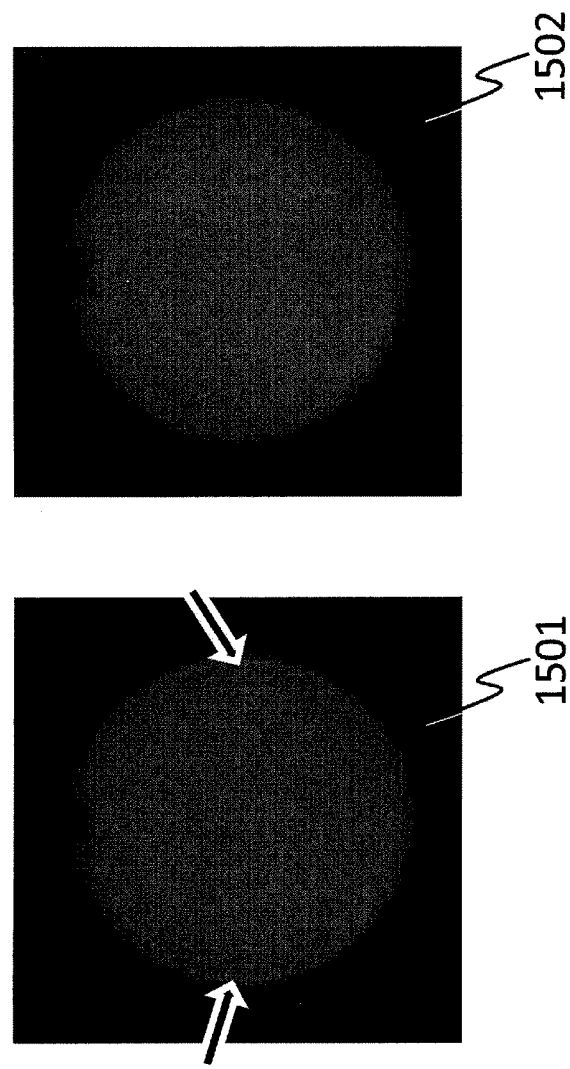
FIG. 15 is a diagram showing reconstructed images before and after processing of recalculating the k-space coordinates.

By repeating the recreation of the input gradient magnetic field waveform in this manner, it is possible to maintain the resolution of the image without reducing the range of k-space coordinates eventually. FIG. 15 is an image 1501 obtained using k-space coordinates before recalculation and an image 1502 obtained using k-space coordinates after recalculation. Both the images are imaging results in EPI measurement, and a readout gradient magnetic field is applied in the horizontal direction in the image. In the image 1502 obtained using the k-space coordinates after recalculation, image distortion indicated by the arrow is small compared with the image 1501 obtained using the k-space coordinates before recalculation. Accordingly, it can be seen that compensation of the distortion of the readout gradient magnetic field is appropriately performed in the image 1502.

Imaging is performed using the high frequency magnetic field pulse modified by the above process 103, and image reconstruction of the acquired NMR signal is performed using the k-space coordinates modified by the above process 104. Therefore, it is possible to obtain an image in which there is no mixing of an external signal with the selected slice and image distortion or artifacts are suppressed.

The advantages of the present embodiment described above over the conventional technique are as follows.

First, in the method of outputting the gradient magnetic field pulse for compensating for the eddy current (PTL 1 and PTL 2), it is difficult and expensive to completely correct a magnetic field due to eddy current showing temporally and spatially high-order complex changes. In contrast, in the present embodiment, no special coil for magnetic field correction is required, and degradation of the excitation profile and image distortion or artifacts, such as ghosting, can be suppressed by recalculating the k-space coordinates and the high frequency magnetic field pulse including a magnetic field due to eddy current.

In addition, in the method of changing the irradiation timing of the high frequency magnetic field pulse according to the output gradient magnetic field waveform (PTL 3), only the irradiation timing of the high frequency magnetic field pulse is changed. In contrast, in the present embodiment, since the output gradient magnetic field waveform is estimated using the response functions of the eddy current and the control circuit of the gradient magnetic field power source, it is possible to compensate for even nonlinear distortion of the output gradient magnetic field waveform.

In the method of using a fixed input gradient magnetic field waveform (NPL 1), only a specific pulse sequence can be applied. In contrast, in the present embodiment, since it is possible to estimate output gradient magnetic field waveforms for all input gradient magnetic field waveforms, there is no limitation that a fixed input gradient magnetic field waveform should be used.

In addition, in the method of modeling the system response using the RLC circuit (NPL 2), the behavior of the control circuit of the gradient magnetic field power source is not taken into consideration. In the present embodiment, however, since the behavior of the control circuit of the gradient magnetic field power source is also taken into consideration, it is possible to recalculate the high frequency magnetic field pulse and the k-space coordinates with higher accuracy. In addition, in the method of modeling the system response using the RCL circuit (NPL 2), each coefficient of the model expression is calculated with the appearance of the image as a criterion of determination. In the present embodiment, however, since the coefficient of the model expression is calculated on the basis of the output gradient magnetic field waveform, it is possible to calculate a high-accuracy model expression without depending on human determination.

In addition, in the method of measuring the gradient magnetic field waveform after imaging and using the measured gradient magnetic field waveform for reconstruction (NPL 3), fluctuations due to noise are superimposed. In the present embodiment, however, since a model expression is prepared to express the eddy current and the control component of the gradient magnetic field power source circuit, noise is not superimposed on the output gradient magnetic field waveform to be estimated.

Second Embodiment

Also in the present embodiment, the configuration of the digital signal processor 8 shown in FIG. 2 and the four characteristic processes 101 to 104 performed by the digital signal processor 8 are the same as those in the first embodiment.

Figure 16:
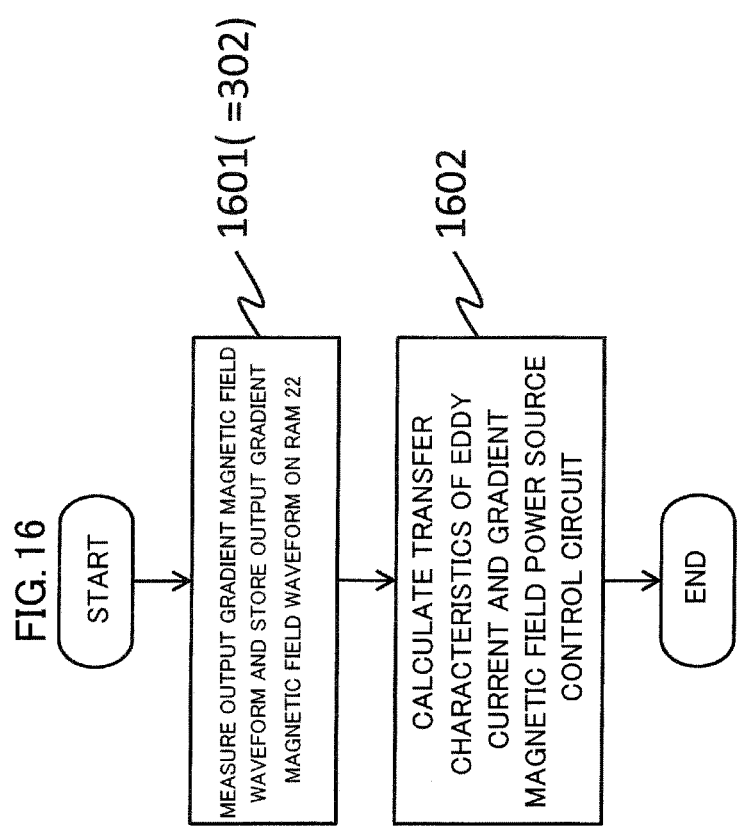
FIG. 16 is a flowchart showing the overall procedure in a second embodiment.

The present embodiment is characterized in that the process 101 of calculating the response functions of the eddy current and the control circuit of the gradient magnetic field power source is performed in a simpler procedure than in the first embodiment. That is, in the first embodiment, measurement of the output gradient magnetic field waveform has been performed twice in a state where the control of the gradient magnetic field power source circuit is disabled and a state where the control of the gradient magnetic field power source circuit is enabled. In the present embodiment, however, the measurement of the output gradient magnetic field waveform is performed only once. The flow of the process of the present embodiment will be described with reference to the flowchart of FIG. 16.

First, in step 1601, the output gradient magnetic field waveform is measured for each space. In this case, the control parameter of the gradient magnetic field power source is not changed, so that the control parameter is in the normal state of the apparatus. That is, the control parameter of the gradient magnetic field power source is enabled. The measurement result of the output gradient magnetic field waveform is stored on the RAM 22. This processing is the same as the processing performed in steps 302 and 305 of FIG. 3 showing the flow of the first embodiment.

Then, in step 1602, the input gradient magnetic field waveform stored on the RAM 22 and the measured output gradient magnetic field waveform are read, and the response functions of the eddy current and the control circuit of the gradient magnetic field power source are calculated.

Figure 17:
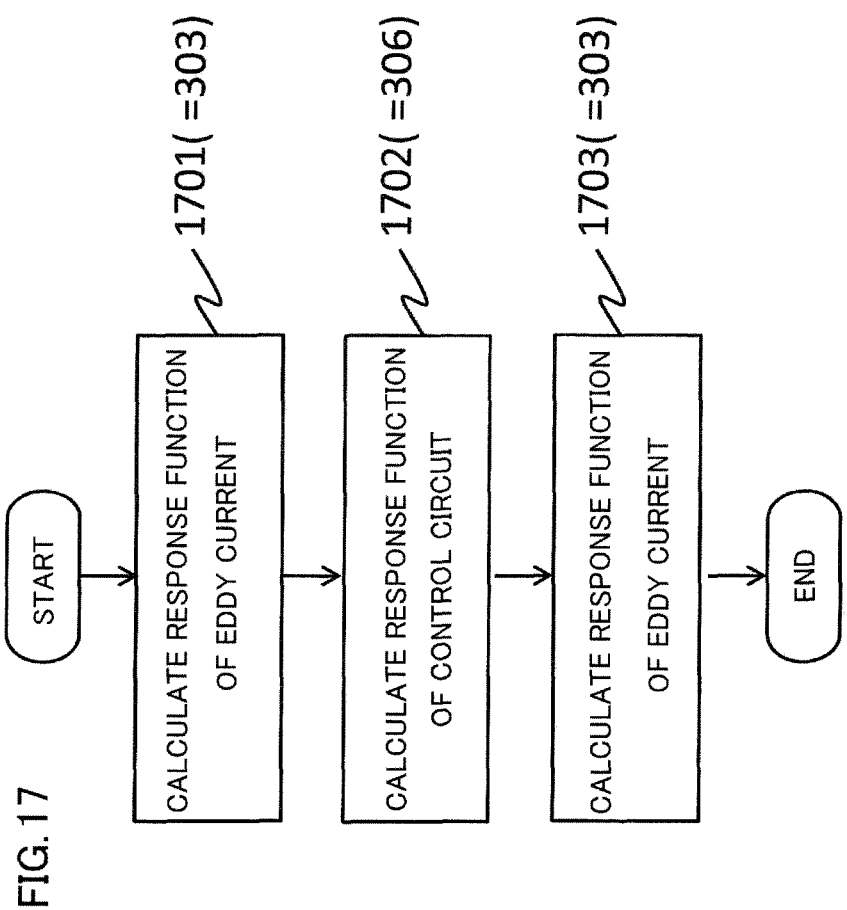
FIG. 17 is a flowchart showing the procedure of response function calculation in the second embodiment.

The calculation of the response functions of the eddy current and the control circuit of the gradient magnetic field power source will be described with reference to the flowchart of FIG. 17. In step 1701, the response function of the eddy current is calculated. This processing is the same as the processing of step 303 in the first embodiment described above. That is, the response function h(t) that minimizes the evaluation amount e1 in the following Expression (31) is searched for.

$$e1 = \sum_t (gout(t) - h'(t) * gin(t))^2 \qquad (31)$$

Here, gout(t) is an output gradient magnetic field waveform stored on the RAM 22 in step 1601, and gin(t) is an input gradient magnetic field waveform. h(t) is a response function of the eddy current defined by Expression (4), and the coefficients $\alpha 1$ to $\alpha n$ and $\tau_1$ to $\tau_n$ of Expression (4) are searched for as in step 303 in the first embodiment.

Expression (31) has the same form as Expression (5) in the first embodiment. However, the output gradient magnetic field waveform gout(t) of Expression (5) is measured in a state where the control circuit of the gradient magnetic field power source is disabled, whereas distortion due to the control circuit of the gradient magnetic field power source is included in the output gradient magnetic field waveform gout(t) of Expression (31). Therefore, not only the eddy current but also the characteristics of the control circuit of the gradient magnetic field power source are included in the calculated response function h(t) of the eddy current.

Then, in step 1702, the response function of the control circuit of the gradient magnetic field power source is calculated. This processing is the same as the processing of step 306 in the first embodiment. That is, gamp(t) that minimizes the evaluation amount e2 in Expression (32) is searched for. gamp(t) in Expression (32) is defined by Expression (33).

$$e2 = \sum_t (gout(t) - h'(t) * gamp(t))^2 \qquad (32)$$

$$gamp(t) = gin(t) + u(t) \qquad (33)$$

Here, u(t) is a control component of the gradient magnetic field power source defined by Expression (9). However, the response component of the control circuit of the gradient magnetic field power source is also included in the response function h(t) of the eddy current calculated in step 1701. Accordingly, a component that could not be expressed in the model (Expression (4)) of the response function of the eddy current is applied to Expression (9) for calculation.

After calculating the response function u(t) of the control circuit of the gradient magnetic field power source in step 1702, in step 1703, the response function h(t) of the eddy current is recalculated. This is because the optimal value of each coefficient ($\alpha_1$ to $\alpha_n$ and $\tau_1$ to $\tau_n$) of the response function h(t) (Expression (4)) of the current is changed due to defining the response function u(t) of the control circuit of the gradient magnetic field power source. The response function h(t) is recalculated by replacing gin(t) in Expression (31) with gamp(t) calculated in step 1702 and searching for each coefficient of h(t) that minimizes the evaluation amount e1. Through the above processing, it is possible to calculate a response function in consideration of the response function of the eddy current and the control component of the gradient magnetic field power source. The response function is calculated for each piece of data measured for each space, and is stored on the RAM 22 of the signal processing system 7.

The procedure of the process 102, which is for estimating the output gradient magnetic field waveform, and the processes 103 and 104, which are for recalculating the high frequency magnetic field pulse or the k-space coordinates, using the response function stored on the RAM 22 at the time of imaging are the same as that in the first embodiment. Accordingly, explanation thereof will be omitted.

According to the present embodiment, the number of calculations of the response function is increased, but the number of measurements of the output gradient magnetic field waveform can be reduced. Therefore, since work to change the control parameter of the gradient magnetic field power source can also be omitted, it is possible to calculate a response function required to recalculate the excitation profile in a simpler procedure. Other effects are the same as those in the first embodiment.

Third Embodiment

Figure 18:
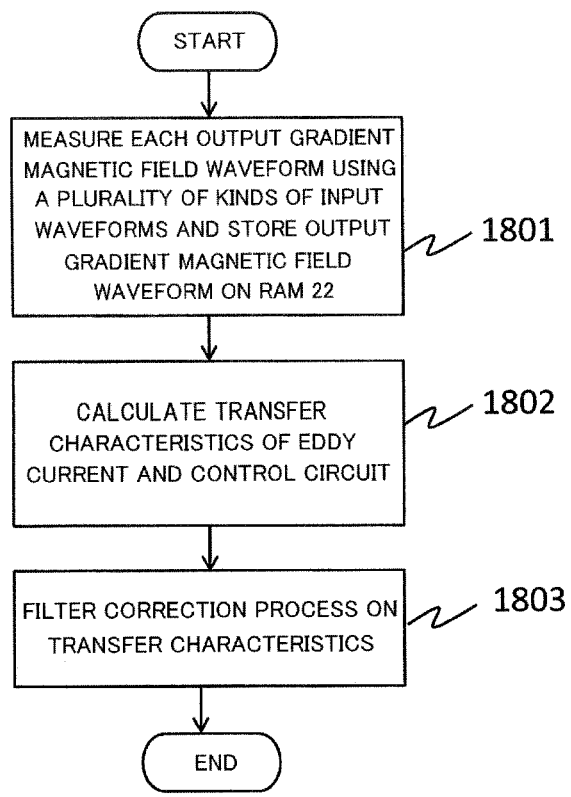
FIG. 18 is a flowchart showing the overall procedure in a third embodiment.

Also in the present embodiment, the configuration of the digital signal processor 8 shown in FIG. 2 and the four processes 101 to 104 performed by the digital signal processor 8 are the same as those in the first embodiment. The present embodiment is characterized in that the response functions of the eddy current and the control circuit of the gradient magnetic field power source are calculated without specific model expressions being applied. FIG. 18 shows the flow of the process of the present embodiment. Although steps 1801 and 1802 in FIG. 18 are the same as the steps 1601 and 1602 in FIG. 16 described in the second embodiment, processing unique to the present embodiment is processing of measuring the output gradient magnetic field waveform using a plurality of kinds of input gradient magnetic field waveforms in step 1801, processing of directly deriving the response functions of the eddy current and the gradient magnetic field control circuit without using any model expression in step 1802, and processing of correcting the derived response function in step 1803.

As described previously, if the input gradient magnetic field waveform Gin(s) (Laplace transform) and the output gradient magnetic field waveform Gout(s) (Laplace transform) are known, the transfer characteristic H(s) of the eddy current can be calculated from Expression (3.1) in theory. Expression (3.1) is written again.

$$H(s) = Gout(s)/Gin(s) \quad (3.1)$$

However, when the value of Gin(s) is 0, the value of H(s) diverges. Accordingly, a correct value is not obtained.

In order to prevent this, in the first and second embodiments, the response function that gives an optimal evaluation value has been derived by applying the response function of the eddy current to the model expression.

In the present embodiment, a response function h(t) calculated from Expression (3.1) or Expression (3.2), which is obtained by an inverse Laplace transform of Expression (3.1), is used without using any model expression. In this case, in order to eliminate the influence of zero points, a plurality of kinds of input gradient magnetic field waveforms used to calculate the response functions of the eddy current and the gradient magnetic field power source control circuit are prepared.

Figure 19:
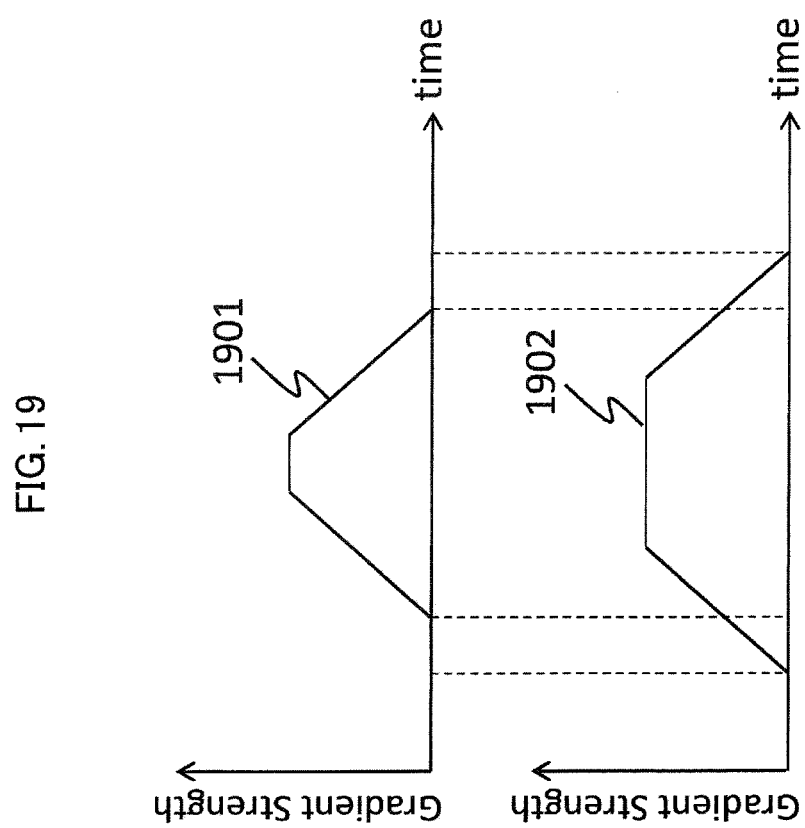
FIG. 19 is a diagram showing an example of an input gradient magnetic field waveform used in the response function calculation process of the third embodiment.

Specifically, in step 1801, each output gradient magnetic field waveform is measured using a plurality of kinds of input gradient magnetic field waveforms, and is stored on the RAM 22. Preferably, the input gradient magnetic field waveform has a steep shape as much as possible. This is because a high frequency region is not included in the waveform of gentle change and accordingly a high-frequency response cannot be calculated. Ideally, it is desirable to use an impulse wave. However, it is difficult to output an impulse wave due to restrictions, such as the output performance of the gradient magnetic field power source. In the present embodiment, therefore, a plurality of trapezoidal waves shown in FIG. 19 are used.

In step 1802, the transfer characteristic H(s) is calculated from Expression (3.1). In this case, zero points are avoided by replacing a zero point, which appears in the spectrum (Laplace transform) of one input gradient magnetic field waveform (trapezoidal wave), using the spectral data of other input gradient magnetic field waveforms (trapezoidal waves). Specifically, the above is performed according to the following expression.

$$H(s) = \begin{cases} Gout1(s)/Gin1(s) & \text{if } (Gin1(s) > Gin2(s)) \\ Gout2(s)/Gin2(s) & \text{if } (Gin2(s) > Gin1(s)) \end{cases} \quad (34)$$

Here, Gin1(s) is a Laplace transform of a trapezoidal wave 1901, Gout1(s) is a Laplace transform of an output gradient magnetic field waveform when the trapezoidal wave 1901 is used as an input gradient magnetic field waveform, Gin2(s) is a Laplace transform of a trapezoidal wave 1902, and Gout2(s) is a Laplace transform of an output gradient magnetic field waveform when the trapezoidal wave 1902 is used as an input gradient magnetic field waveform.

FIG. 20 shows the outline of the amplitude spectrum obtained by the Laplace transform of the trapezoidal wave group shown in FIG. 19. As shown in FIG. 20, positions where zero points appear in the spectra 2001 and 2002 of the trapezoidal waves 1901 and 1902 are different between the spectra 2001 and 2002. Therefore, as shown in Expression (34), zero points can be avoided by performing calculation using the spectrum having a larger value. In addition, although two trapezoidal waves are shown in FIG. 19, it is also possible to prepare three or more trapezoidal waves. In this case, it is preferable to select a combination of an input gradient magnetic field waveform in which the value of the spectrum is largest (there is no zero point), among a plurality of input gradient magnetic field waveforms, and an output gradient magnetic field waveform according to the input gradient magnetic field waveform and use the combination for the calculation of the transfer characteristic in Expression (34).

Then, in step 1803, processing of eliminating the influence of noise from the response function h(t) calculated in step 1802 is performed. This is because noise is superimposed since Gout1(s) and Gout2(s) are measured data and accordingly a correct transfer characteristic may not be calculated. In the present embodiment, such noise is removed by performing a two-step filtering process in Laplace space.

First, the transfer characteristic calculated by Expression (34) is multiplied by an optimal filter of the following expression, thereby suppressing the influence of noise.

$$H'(s)=H(s)\times\Phi(s) \quad (35)$$

Here, H'(s) is a transfer characteristic after optimal filter application, and φ(s) is an optimal filter. As the optimal filter φ(s), a Wiener filter that is a known technique is used. The Wiener filter is defined by the following expression.

$$\Phi(s) = \frac{|S(s)|^2}{|S(s)|^2 + |N(s)|^2} \quad (36)$$

Here, N(s) is a noise component of Gout1(s), and S(s) is a signal component excluding the noise of Gout1(s). As methods of calculating N(s) and S(s), according to a known technique, the signal value of the highest frequency of the power spectrum of Gout1(s) is set as N(s), and S(s) is obtained by subtracting N(s) from the power spectrum of Gout1(s).

Although the influence of noise can be reduced to some extent by such an optimal filter, the influence of noise may cause a problem even after optimal filter application in practice. Therefore, a noise removal filter is applied to the transfer characteristic after optimal filter application. In the present embodiment, a median filter is used as a noise removal filter.

$$H''(s)=\mathrm{median}(H'(s)) \quad (37)$$

Here, H"(s) is a transfer characteristic after median filter application.

Finally, a response function of the eddy current and the gradient magnetic field power source control circuit that are combined is obtained by the inverse Laplace transform of Expression (37).

$$h(t)=\mathrm{ILT}[H''(s)] \quad (38)$$

Here, ILT[ ] indicates an inverse Laplace transform.

The procedure of estimating the output gradient magnetic field waveform and recalculating the high frequency magnetic field pulse and the k-space coordinates using the response function calculated as described above is the same as that in the first embodiment.

Thus, in the present embodiment, response functions can be calculated without specific model expressions being applied by reducing the noise, which is included in measured data, by two filter processes in Laplace space. Accordingly, flexible applications to various hardware configurations (gradient magnetic field coil and the like) and software configurations (gradient magnetic field power source control method) can be made.

While the operation of the MRI apparatus of the present invention, in particular, each embodiment of the operation of the unit that calculates a response function of the gradient magnetic field has been described above, the present invention is not limited to the embodiments described above, and various changes can be made. For example, model expressions that express the distortion of the output gradient magnetic field waveform due to eddy current or the distortion of the output gradient magnetic field waveform due to the control circuit of the gradient magnetic field power source are not limited to those exemplified in the embodiments, and other model expressions can also be used. In addition, in the above embodiments, the case has been described in which the eddy current and the control circuit of the gradient magnetic field power source are adopted as causes of distorting the output gradient magnetic field waveform and their response functions are used to calculate the output gradient magnetic field waveform. However, other elements, for example, other components, such as a residual magnetic field with hysteresis seen in the MRI apparatus using a permanent magnet, can also be added for the calculation of the output gradient magnetic field waveform. In addition, the procedure of the flowchart shown for illustration of each embodiment is an example, and processes may be omitted, or it is also possible to add other processes as necessary.

The present invention can be appropriately applied to the case where the high frequency magnetic field pulse is calculated by the output gradient magnetic field waveform calculated for the slice gradient magnetic field or the case where the k-space coordinates, at which the NMR signal is disposed, are corrected by the output gradient magnetic field waveform calculated for the readout gradient magnetic field. However, the present invention can also be applied to the phase encoding gradient magnetic field. In addition, a two-direction gradient magnetic field in a pulse sequence, such as a radial scan or a spiral scan without distinction of a readout gradient magnetic field and a phase encoding gradient magnetic field, is also included in the readout gradient magnetic field.

In addition, although the case where the output gradient magnetic field waveform is estimated for both the slice gradient magnetic field and the readout gradient magnetic field and both the recalculation of the high frequency magnetic field pulse and the recalculation of the k-space coordinates are performed has been described in the above embodiment, a case where only one of the recalculation of the high frequency magnetic field pulse and the recalculation of the k-space coordinates is performed is also included in the present invention.

An overview of the present invention that will become apparent in the description of each of the above embodiments is as follows. That is, an MRI apparatus of the present invention includes: an imaging unit including a static magnetic field generation section, a gradient magnetic field generation section, a high frequency magnetic field generation section, and a high frequency magnetic field detection section; a control unit that controls an operation of the imaging unit on the basis of an imaging sequence; and a calculation unit that performs calculation including image reconstruction using a nuclear magnetic resonance signal detected by the high frequency magnetic field detection section. The calculation unit includes: a response function calculation section that calculates, using an input waveform input to the gradient magnetic field generation section and an output waveform that the gradient magnetic field generation section generates using the input waveform, a response function that is a sum of response functions of a plurality of elements affecting the output waveform; a gradient magnetic field calculation section that calculates an output waveform from an input waveform of a gradient magnetic field pulse, which is set in the imaging sequence, using the response function calculated by the response function calculation section; and a compensation section that modifies a high frequency magnetic field pulse, which is set in the imaging sequence, and/or modifies k-space coordinates of a nuclear magnetic resonance signal, which is obtained in the imaging sequence, using a calculated value of the output waveform calculated by the gradient magnetic field calculation section.

Preferably, the response function calculation section calculates a response function for each of the plurality of elements that changes the output waveform, and the gradient magnetic field calculation section calculates an output waveform using a response function that is a sum of response functions of the plurality of elements.

In addition, preferably, the response function calculation section includes a model setting section that sets a response function model for each of the elements and a model optimization section that optimizes the response function model so that a difference between a calculated value of an output waveform calculated by the response function model set by the model setting section and a measured value of the output waveform is minimized, and the response function model optimized by the model optimization section is set as a response function of each element.

In addition, preferably, the response function calculation section uses a plurality of input values as the input value, and calculates a response function directly from a relationship between each input value and a measured value of an output waveform using a combination of the plurality of input values and measured values corresponding to the input values.

In addition, preferably, the response function calculation section includes a filter section that filters a response function after calculation.

In addition, preferably, the filter section includes a Wiener filter and a median filter.

In addition, preferably, the gradient magnetic field generation section includes a control circuit that controls an input waveform based on an output waveform of a generated gradient magnetic field, and the plurality of elements that changes the output waveform includes distortion of the output waveform due to control of the control circuit.

In addition, preferably, the response function calculation section calculates a response function for each of a plurality of gradient magnetic fields having different positions with respect to a center of a static magnetic field generated by the static magnetic field generation section.

In addition, preferably, a gradient magnetic field pulse calculated by the gradient magnetic field calculation section is a slice selection gradient magnetic field in the imaging sequence, and the compensation section includes a high frequency pulse correction section that corrects a high frequency pulse, which is set in the imaging sequence, on the basis of a calculated value of the slice selection gradient magnetic field.

In addition, preferably, the high frequency pulse correction section includes an irradiation time calculation section that calculates a change in irradiation time of high frequency pulses before and after correction, and changes an input value of the gradient magnetic field calculation section when the change in irradiation time calculated by the irradiation time calculation section exceeds a predetermined increase rate and corrects the high frequency pulse using an estimated value of an output waveform estimated from the changed input value by the gradient magnetic field calculation section.

In addition, preferably, a gradient magnetic field pulse calculated by the gradient magnetic field calculation section is a readout gradient magnetic field in the imaging sequence, and the compensation section includes a k-space coordinate correction section that corrects k-space coordinates, in which the nuclear magnetic resonance signal obtained in the imaging sequence is disposed, on the basis of a calculated value of the readout selection gradient magnetic field.

In addition, preferably, the correction section includes a k-space size calculation section that calculates a change in size of k-space coordinates before and after correction, and changes an input value of the gradient magnetic field calculation section when the change in size of k-space calculated by the k-space size calculation section exceeds a predetermined reduction rate and corrects the k-space coordinates using a recalculated value of an output waveform calculated from the changed input value by the gradient magnetic field calculation section.

A method for estimating an output gradient magnetic field waveform generated by a gradient magnetic field generation section of a magnetic resonance imaging apparatus of the present invention includes: inputting an input value of the gradient magnetic field generation section and a measured value of an output gradient magnetic field waveform that the gradient magnetic field generation section generates using the input value; setting a response function model for each of a plurality of factors affecting the output gradient magnetic field waveform; a step of optimizing each response function model using the input value and the measured value of the gradient magnetic field waveform that have been input; and calculating an estimated value of an output gradient magnetic field waveform with respect to an input value of a desired gradient magnetic field using the optimized response function model.

Preferably, the plurality of factors includes an eddy current generated by a gradient magnetic field and an output of a control circuit provided in the gradient magnetic field generation section.

In addition, preferably, the measured value includes a first measured value when the control circuit of the gradient magnetic field generation section is disabled and a second measured value when the control circuit is enabled, and in the step of optimizing the response function model, a response function of an output gradient magnetic field waveform due to the control circuit is calculated using the first and second measured values.

In addition, another method for estimating an output gradient magnetic field waveform generated by a gradient magnetic field generation section of a magnetic resonance imaging apparatus of the present invention includes: inputting at least two kinds of input values of the gradient magnetic field generation section and measured values of an output gradient magnetic field waveform that the gradient magnetic field generation section generates using the input values; calculating a response function of the gradient magnetic field generation section, which includes effects of a plurality of factors affecting the output gradient magnetic field waveform, using the at least two kinds of input values and measured values corresponding to the input values; and calculating an estimated value of an output gradient magnetic field waveform with respect to an input value of a desired gradient magnetic field using the response function are included.

INDUSTRIAL APPLICABILITY

According to the present invention, in the MRI apparatus, it is possible to compensate for the distortion of the output gradient magnetic field waveform caused by various factors with high accuracy without adding a heavy load. As a result, it is possible to provide a highly reliable image with no image distortion or no artifacts, such as ghosting.

REFERENCE SIGNS LIST

1: object
2: static magnetic field generation system
3: gradient magnetic field generation system
4: sequencer
5: signal transmission system
6: signal receiving system
7: signal processing system
8: digital signal processor (CPU)
9: gradient magnetic field coil
10: gradient magnetic field power source
11: high frequency oscillator
12: modulator
13: high frequency amplifier
14a: high frequency coil (transmission coil)
14b: high frequency coil (receiving coil)
15: signal amplifier
16: quadrature phase detector
17: A/D converter
18: magnetic disk
19: optical disc
20: display
21: ROM
22: RAM
23: track ball or mouse
24: keyboard
25: operating unit
81: response function calculation unit
82: gradient magnetic field waveform calculation unit
83: sequence calculation unit
84: k-space coordinate calculation unit
85: image reconstruction unit

The invention claimed is:

1. A method for estimating an output gradient magnetic field waveform in a magnetic resonance imaging apparatus, the gradient magnetic field waveform estimating method comprising:
inputting at least two kinds of input values to a gradient magnetic field generation section and measuring output values of an output gradient magnetic field waveform that the gradient magnetic field generation section generates using the input values, in a state in which a control parameter of the gradient magnetic field generation section is disabled so that an operation is not performed by the gradient magnetic field generation section;
calculating a response function of the gradient magnetic field generation section, which includes effects of a plurality of factors affecting the output gradient magnetic field waveform, using the at least two kinds of input values and measured output values corresponding to the input values; and
calculating an estimated value of an output gradient magnetic field waveform with respect to an input value of a desired gradient magnetic field using the response function.

2. A method for estimating an output gradient magnetic field waveform generated by a gradient magnetic field generation section of a magnetic resonance imaging apparatus, the gradient magnetic field waveform estimating method comprising:
inputting an input value to the gradient magnetic field generation section and measuring an output value of an output gradient magnetic field waveform that the gradient magnetic field generation section generates using the input value, in a state in which a control parameter of the gradient magnetic field generation section is disabled so that an operation is not performed by the gradient magnetic field generation section;
setting a response function model for each of a plurality of factors affecting the output gradient magnetic field waveform;
optimizing each response function model using the input value and the output value; and
calculating an estimated value of an output gradient magnetic field waveform with respect to an input value of a desired gradient magnetic field using the optimized response function model.

3. The gradient magnetic field waveform estimating method according to claim 2,
wherein the plurality of factors includes an eddy current generated by a gradient magnetic field and an output of a control circuit provided in the gradient magnetic field generation section.

4. The gradient magnetic field waveform estimating method according to claim 3,
wherein the measured value includes a first measured value when the control circuit of the gradient magnetic field generation section is disabled and a second measured value when the control circuit is enabled, and
in the step of optimizing the response function model, a response function of an output gradient magnetic field waveform due to the control circuit is calculated using the first and second measured values.

5. A magnetic resonance imaging apparatus, comprising:
an imaging unit including a static magnetic field generation section, a gradient magnetic field generation section, a high frequency magnetic field generation section, and a high frequency magnetic field detection section;
a control unit that controls an operation of the imaging unit on the basis of an imaging sequence, and inputs an input waveform to the gradient magnetic field generation section, and measures an output waveform that the gradient magnetic field generation section generates in response to the input waveform, in a state in which a control parameter of the gradient magnetic field generation section is disabled so that an operation is not performed by the gradient magnetic field generation section; and
a calculation unit that performs calculation including image reconstruction using a nuclear magnetic resonance signal detected by the high frequency magnetic field detection section, wherein the calculation unit includes:
a response function calculation section that calculates, using the input waveform and the output waveform, a response function that is a sum of response functions of a plurality of elements affecting the output waveform;
a gradient magnetic field calculation section that calculates an output waveform from an input waveform of a gradient magnetic field pulse, which is set in the imaging sequence, using the response function calculated by the response function calculation section; and
a compensation section that modifies a high frequency magnetic field pulse, which is set in the imaging sequence, and/or modifies k-space coordinates of a nuclear magnetic resonance signal, which is obtained in the imaging sequence, using a calculated value of the output waveform calculated by the gradient magnetic field calculation section.

6. The magnetic resonance imaging apparatus according to claim 5,
wherein the response function calculation section calculates a response function for each of the plurality of elements that changes the output waveform, and
the gradient magnetic field calculation section calculates an output waveform using a response function that is a sum of response functions of the plurality of elements.

7. The magnetic resonance imaging apparatus according to claim 6,
wherein the response function calculation section includes a model setting section that sets a response function model for each of the elements and a model optimization section that optimizes the response function model so that a difference between a calculated value of an output waveform calculated by the response function model set by the model setting section and a measured value of the output waveform is minimized, and
the response function model optimized by the model optimization section is set as a response function of each element.

8. The magnetic resonance imaging apparatus according to claim 5,
wherein the response function calculation section uses a plurality of input values as the input waveform, and calculates a response function directly from a relationship between each input value and a measured value of an output waveform using a combination of the plurality of input values and measured values corresponding to the input values.

9. The magnetic resonance imaging apparatus according to claim 8,
wherein the response function calculation section includes a filter section that filters a response function after calculation.

10. The magnetic resonance imaging apparatus according to claim 9,
wherein the filter section includes a Wiener filter and a median filter.

11. The magnetic resonance imaging apparatus according to claim 5,
wherein the gradient magnetic field generation section includes a control circuit that controls an input waveform based on an output waveform of a generated gradient magnetic field, and
the plurality of elements that changes the output waveform includes distortion of the output waveform due to control of the control circuit.

12. The magnetic resonance imaging apparatus according to claim 5,
wherein the response function calculation section calculates a response function for each of a plurality of gradient magnetic fields having different positions with respect to a center of a static magnetic field generated by the static magnetic field generation section.

13. The magnetic resonance imaging apparatus according to claim 5,
wherein a gradient magnetic field pulse calculated by the gradient magnetic field calculation section is a slice selection gradient magnetic field in the imaging sequence, and
the compensation section includes a high frequency pulse correction section that corrects a high frequency pulse, which is set in the imaging sequence, on the basis of a calculated value of the slice selection gradient magnetic field.

14. The magnetic resonance imaging apparatus according to claim 13,
wherein the high frequency pulse correction section includes an irradiation time calculation section that calculates a change in irradiation time of high frequency pulses before and after correction, and changes an input value of the gradient magnetic field calculation section when the change in irradiation time calculated by the irradiation time calculation section exceeds a predetermined increase rate and corrects the high frequency pulse using an estimated value of an output waveform estimated from the changed input value by the gradient magnetic field calculation section.

15. The magnetic resonance imaging apparatus according to claim 5,
wherein a gradient magnetic field pulse calculated by the gradient magnetic field calculation section is a readout gradient magnetic field in the imaging sequence, and
the compensation section includes a k-space coordinate correction section that corrects k-space coordinates, in which the nuclear magnetic resonance signal obtained in the imaging sequence is disposed, on the basis of a calculated value of the readout gradient magnetic field.

16. The magnetic resonance imaging apparatus according to claim 15,
wherein the k-space coordinate correction section includes a k-space size calculation section that calculates a change in size of k-space coordinates before and after correction, and changes an input value of the gradient magnetic field calculation section when the change in size of k-space coordinates calculated by the k-space size calculation section exceeds a predetermined reduction rate and corrects the k-space coordinates using a recalculated value of an output waveform calculated from the changed input value by the gradient magnetic field calculation section.

* * * * *